(12) United States Patent
Nagai et al.

(10) Patent No.: US 11,047,798 B2
(45) Date of Patent: Jun. 29, 2021

(54) MEASUREMENT METHOD, MEASUREMENT APPARATUS, AND MEASUREMENT SYSTEM

(71) Applicant: Konica Minolta, Inc., Tokyo (JP)

(72) Inventors: Fumio Nagai, Hachioji (JP); Tetsuya Noda, Hino (JP); Hideyuki Fujii, Yoshikawa (JP)

(73) Assignee: KONICA MINOLTA, INC., Tokyo (JP)

( * ) Notice: Subject to any disclaimer, the term of this patent is extended or adjusted under 35 U.S.C. 154(b) by 246 days.

(21) Appl. No.: 16/322,832

(22) PCT Filed: Aug. 1, 2017

(86) PCT No.: PCT/JP2017/027868
§ 371 (c)(1),
(2) Date: Feb. 1, 2019

(87) PCT Pub. No.: WO2018/034143
PCT Pub. Date: Feb. 22, 2018

(65) Prior Publication Data
US 2020/0182784 A1  Jun. 11, 2020

(30) Foreign Application Priority Data
Aug. 18, 2016 (JP) .............................. JP2016-160753

(51) Int. Cl.
*G01N 21/41* (2006.01)
*B01L 3/00* (2006.01)
(Continued)

(52) U.S. Cl.
CPC .............. *G01N 21/41* (2013.01); *B01L 3/502* (2013.01); *G01N 21/648* (2013.01);
(Continued)

(58) Field of Classification Search
CPC ..... B01L 2300/0663; B01L 2300/0877; B01L 2300/12; B01L 2300/168; G01N 33/49; G01N 33/543
See application file for complete search history.

(56) References Cited

U.S. PATENT DOCUMENTS 7,593,108 B2 * 9/2009 Sterling ............. A61B 5/14546
356/39

FOREIGN PATENT DOCUMENTS

| EP | 2136210 A1 | 12/2009 |
| JP | 3586743 B2 | 4/1997 |

(Continued)

OTHER PUBLICATIONS

Tokuda et al, CMOS image sensor-based implantable glucose sensor using glucose-responsive fluorescent hydrogel, Biomedical Optics Express, Oct. 10, 2014 vol. 5, No. 11 (Year: 2014).*

(Continued)

*Primary Examiner* — Jennifer Wecker
*Assistant Examiner* — Jonathan Bortoli
(74) *Attorney, Agent, or Firm* — Lucas & Mercanti, LLP

(57) ABSTRACT

A specimen containing a substance to be measured is introduced into a flow path of a measurement chip including a flow path which is a cavity for accommodating liquid and a reflecting unit which specularly reflects light which passes through the flow path so as to pass through the flow path again and a measurement value indicating an amount of the substance to be measured in the specimen is acquired. Then, second light acquired when first light including light of a wavelength absorbed by a red blood cell passes through the specimen in the flow path, is reflected by the reflecting unit, and passes through the specimen in the flow path again is detected in a state in which the specimen is present in the flow path. Next, a hematocrit value of the specimen is (Continued)

determined on the basis of a detection result of the second light. Next, a measurement value is corrected on the basis of the hematocrit value.

20 Claims, 9 Drawing Sheets

(51) Int. Cl.
*G01N 21/64* (2006.01)
*G01N 33/49* (2006.01)
*G01N 33/543* (2006.01)
*G01N 33/553* (2006.01)

(52) U.S. Cl.
CPC ... *G01N 33/4915* (2013.01); *G01N 33/54366* (2013.01); *G01N 33/553* (2013.01); *B01L 2300/0663* (2013.01); *B01L 2300/0877* (2013.01); *B01L 2300/12* (2013.01); *B01L 2300/168* (2013.01)

(56) References Cited

FOREIGN PATENT DOCUMENTS

| | | | | | |
|---|---|---|---|---|---|
| JP | H09-105750 A | 4/1997 | | | |
| JP | H1-104114 A | 4/1999 | | | |
| JP | 2004-097782 A | 4/2004 | | | |
| JP | 2009-236487 A | 10/2009 | | | |
| JP | 2012-088299 A | 5/2012 | | | |
| WO | 2014/049704 A1 | 4/2014 | | | |
| WO | WO2014/049704 | * | 4/2014 | ............ | G01N 33/52 |
| WO | 2015/129615 A1 | 9/2015 | | | |
| WO | WO2015/129615 | * | 9/2015 | ............ | G01N 21/64 |
| WO | 2016/039149 | 3/2016 | | | |

OTHER PUBLICATIONS

International Search Report dated Sep. 5, 2017 from International Application No. PCT/JP2017/027868 and English translation.
Written Opinion of the International Searching Authority dated Sep. 5, 2017 from International Application No. PCT/JP2017/027868 and English translation.
Extended European Search Report dated Jun. 3, 2019 issued for the corresponding European Patent Application No. 17841370.4 (13 pages).
Office Action (Notice of Reasons for Refusal) dated Sep. 8, 2020 for corresponding Japanese Application No. 2018-534326 with English translation (14 pages).

* cited by examiner

US 11,047,798 B2

MEASUREMENT METHOD, MEASUREMENT APPARATUS, AND MEASUREMENT SYSTEM

This application is a 371 of International Application No. PCT/JP2017/027868 filed on Aug. 1, 2017, which claimed the priority of Japanese Application No. 2016-160753 filed on Aug. 18, 2016, both applications are incorporated herein by reference.

TECHNICAL FIELD

The present invention relates to a measurement method, a measurement apparatus, and a measurement system for measuring a substance to be measured in a specimen containing blood.

BACKGROUND ART

In clinical examinations, if it is possible to quantitatively detect a fine amount of substance to be measured in a specimen such as protein or DNA at high sensitivity, it becomes possible to rapidly grasp a condition of a patient and treat. For example, in a case of measuring an antigen (substance to be measured) in the blood, whole blood collected from the patient or plasma or serum obtained by separating blood cell components from the whole blood may be used as the specimen. In addition, in order to grasp the condition of the patient, it is necessary to measure an amount (concentration) of the substance to be measured with respect to the plasma or serum. However, since a proportion of the plasma or serum to the whole blood varies from patient to patient, in a case where a measurement value indicating the amount of the substance to be measured is acquired by using the whole blood as the specimen, it is necessary to correct the measurement value according to a ratio of the plasma or serum to the whole blood. At that time, a hematocrit value may be used for correcting the measurement value. A method of determining the amount of the substance to be measured on the basis of the hematocrit value and the above-described measurement value is conventionally known (for example, refer to Patent Literature 1).

In the measurement method disclosed in Patent Literature 1, coloration reaction of the blood in the specimen and a dye is utilized. First, absorbance of the specimen is measured by first light having an absorption wavelength specific to hemoglobin and second light having an absorption wavelength specific to the dye. The hematocrit value is determined on the basis of the absorbance of the specimen with respect to the first light and the absorbance of the specimen with respect to the second light. The measurement value indicating the amount of the substance to be measured in the plasma or serum is determined on the basis of the determined hematocrit value and the absorbance of the specimen with respect to the second light.

CITATION LIST

Patent Literature

Patent Literature 1: JP 2009-236487 A

SUMMARY OF INVENTION

Technical Problem

In the measurement method disclosed in Patent Literature 1, the absorbance is measured in a state in which the specimen is absorbed by test paper. Since a microstructure of each test paper differs, scattering of the light (first light and second light) by the test paper fluctuates and there is a case in which the absorbance cannot be measured with a high degree of accuracy. In addition, the first light and the second light are absorbed by the dye, sometimes making it impossible to measure the absorbance with a high degree of accuracy. Therefore, the measurement method disclosed in Patent Literature 1 has a problem that the hematocrit value cannot be determined with a high degree of accuracy.

From a viewpoint of determining the hematocrit value with a higher degree of accuracy, it is conceivable to increase an optical path length in the specimen by increasing a thickness of the test paper to increase the amount of light absorbed by the specimen. However, in this method, contribution of scattering by the test paper and absorption by the dye becomes large, so that it is difficult to improve the measurement accuracy of the hematocrit value.

An object of the present invention is to provide a measurement method, a measurement apparatus, and a measurement system capable of highly accurately determining a hematocrit value and measuring an amount of a substance to be measured in a specimen containing blood with a high degree of accuracy.

Solution to Problem

In order to solve the above-described problem, a measurement method according to one embodiment of the present invention is a measurement method for measuring an amount of a specimen containing blood including a step of introducing the specimen containing the substance to be measured into a flow path of a measurement chip including the flow path which is a cavity for accommodating liquid and a reflecting unit for specularly reflecting light which passes through the flow path so as to pass through the flow path again and acquiring a measurement value indicating the amount of the substance to be measured in the specimen, a step of detecting second light acquired when first light including light of a wavelength absorbed by a red blood cell passes through the specimen in the flow path, is reflected by the reflecting unit, and passes through the specimen in the flow path again in a state in which the specimen is present in the flow path, a step of determining a hematocrit value of the specimen on the basis of a detection result of the second light, and a step of correcting the measurement value on the basis of the hematocrit value.

In order to solve the above-described problem, a measurement apparatus according to one embodiment of the present invention is a measurement apparatus for measuring an amount of a substance to be measured in a specimen containing blood including a chip holder for holding a measurement chip including a flow path which is a cavity for accommodating liquid, and a reflecting unit for specularly reflecting light which passes through the flow path so as to pass through the flow path again, a measurement value acquiring unit for acquiring a measurement value indicating the amount of the substance to be measured in the specimen in a state in which the substance to be measured in the specimen is present in the flow path of the measurement chip held by the chip holder, a light emitting unit for emitting first light including light of a wavelength absorbed by a red blood cell, a light detecting unit for detecting second light acquired when the first light passes through the specimen in the flow path, is reflected by the reflecting unit, and passes through the specimen in the flow path again when the light emitting unit emits the first light toward the reflecting unit in a state in which the specimen is present in the flow path, and a processing unit which determines a hematocrit value of the specimen on the basis of a detection result of the second light by the light detecting unit and corrects the measurement value on the basis of the hematocrit value.

In order to solve the above-described problem, a measurement system according to one embodiment of the present invention is a measurement system for measuring an amount of a substance to be measured in a specimen containing blood, the measurement system including a measurement chip including a flow path which is a cavity for accommodating liquid, and a reflecting unit for specularly reflecting light which passes through the flow path so as to pass through the flow path again, a measurement value acquiring unit for acquiring a measurement value indicating the amount of the substance to be measured in the specimen in a state in which the substance to be measured in the specimen is present in the flow path, a light emitting unit for emitting first light including light of a wavelength absorbed by a red blood cell, a light detecting unit for detecting second light acquired when the first light passes through the specimen in the flow path, is reflected by the reflecting unit, and passes through the specimen in the flow path again when the light emitting unit emits the first light toward the reflecting unit in a state in which the specimen is present in the flow path, and a processing unit which determines a hematocrit value of the specimen on the basis of a detection result of the second light by the light detecting unit and corrects the measurement value on the basis of the hematocrit value.

Advantageous Effects of Invention

According to the present invention, the hematocrit value may be determined with a high degree of accuracy, and the amount of the substance to be measured in the specimen containing blood may be measured with a high degree of accuracy.

DESCRIPTION OF EMBODIMENTS

An embodiment of the present invention is hereinafter described in detail with reference to the drawings. Herein, as a representative example of a measurement apparatus and a measurement system according to the present invention, a measurement apparatus utilizing surface plasmon-field enhanced fluorescence spectroscopy (hereinafter abbreviated as "SPFS") and a measurement system are described.

First Embodiment (Measurement System)

Figure 1:
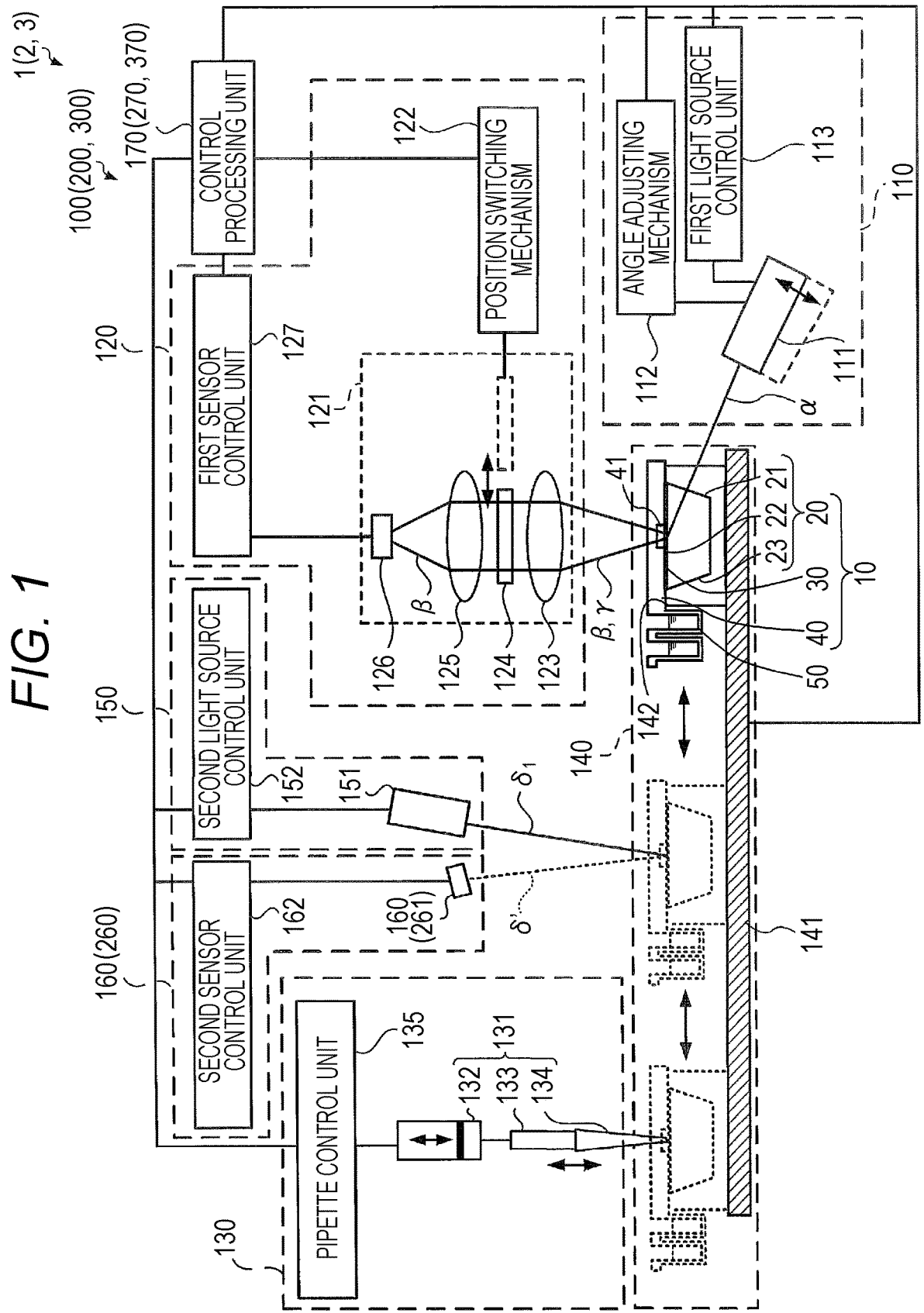
FIG. 1 is a schematic diagram illustrating an example of a configuration of a measurement system according to first to third embodiments.

FIG. 1 is a schematic diagram illustrating an example of a configuration of a measurement system 1 according to a first embodiment. The measurement system 1 according to this embodiment includes a measurement chip 10 and an SPFS apparatus 100. The measurement system 1 is a system for measuring an amount of a substance to be measured in a specimen containing blood.

As illustrated in FIG. 1, the SPFS apparatus 100 includes an excitation light emitting unit (referred to as a "second light emitting unit" in claims) 110, a signal detecting unit 120, a liquid sending unit 130, a transporting unit 140, a light emitting unit 150, a light detecting unit 160, and a control processing unit (processing unit) 170. In the first embodiment, the excitation light emitting unit 110 and the signal detecting unit 120 together form a measurement value acquiring unit for acquiring a measurement value indicating the amount of the substance to be measured in the specimen. The light emitting unit 150 and the light detecting unit 160 form a hematocrit value acquiring unit for acquiring a hematocrit value of the specimen.

Figure 2:
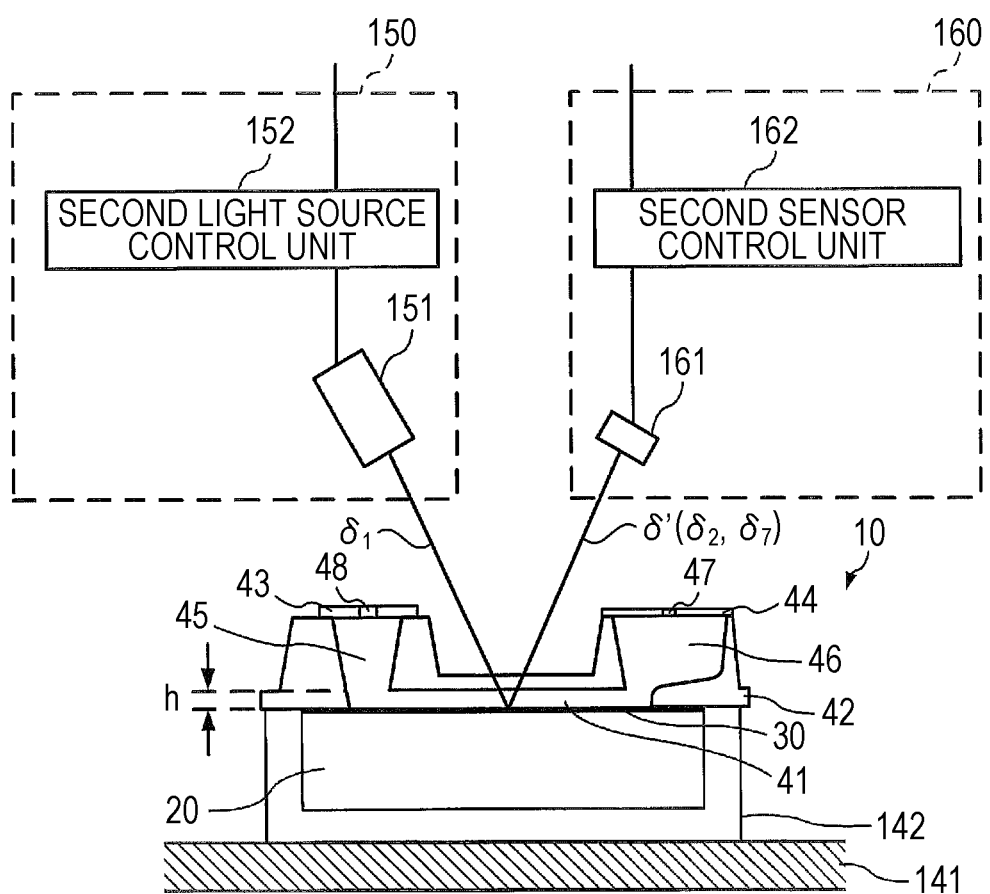
FIG. 2 is a schematic cross-sectional view illustrating a configuration of a hematocrit value acquiring unit in the measurement system according to the first embodiment.

FIG. 2 is a schematic cross-sectional view illustrating a configuration of the hematocrit value acquiring unit in the measurement system 1 according to the first embodiment. FIG. 2 is a view as seen in a normal direction with respect to a plane perpendicular to a paper surface of FIG. 1. In FIG. 1, the light emitting unit 150 and the light detecting unit 160 are arranged along the paper surface for the sake of convenience, but the light emitting unit 150 and the light detecting unit 160 are arranged in a direction perpendicular to the paper surface of FIG. 1 as illustrated in FIG. 2. In FIG. 2, in order to illustrate an optical path in the measurement chip 10, a cross-section of the measurement chip 10 is not hatched. Note that, in FIG. 1, an optical axis of light δ' is indicated by a dotted line for illustrating that an optical axis of light $δ_1$ and the optical axis of the light δ' are included within the plane perpendicular to the paper surface of FIG. 1.

The SPFS apparatus 100 is used in a state in which the measurement chip 10 is attached to a chip holder (holder) 142 of the transporting unit 140. Therefore, the measurement chip 10 is described first, and then the SPFS apparatus 100 is described.

(Measurement Chip)

The measurement chip 10 includes a prism 20, a metal film 30, and a flow path lid 40. In this embodiment, the flow path lid 40 of the measurement chip 10 is integrated with a liquid chip 50 to be described later.

The prism 20 includes an incident surface 21, a film depositing surface 22, and an emitting surface 23. The incident surface 21 allows excitation light α (referred to as "eighth light" in claims) from the excitation light emitting unit 110 to enter the prism 20. The metal film 30 is arranged on the film depositing surface 22. The excitation light α entering the prism 20 is reflected by an interface (film depositing surface 22) between the prism 20 and the metal film 30 to become reflected light. The emitting surface 23 emits the reflected light out of the prism 20.

A shape of the prism 20 is not especially limited. In this embodiment, the shape of the prism 20 is a columnar body having a trapezoid as a bottom surface. A surface corresponding to one bottom side of the trapezoid is the film depositing surface 22, a surface corresponding to one leg is the incident surface 21, and a surface corresponding to the other leg is the emitting surface 23. The trapezoid as the bottom surface is preferably an isosceles trapezoid. As a result, the incident surface 21 and the emitting surface 23 become symmetrical, and an S wave component of the excitation light α is less likely to stay in the prism 20.

The incident surface 21 is formed such that the excitation light α from the excitation light emitting unit 110 is not reflected by the incident surface 21 to return to the excitation light emitting unit 110. In a case where a light source of the excitation light α is a laser diode (hereinafter also referred to as "LD"), when the excitation light α returns to the LD, an excited state of the LD is disturbed and a wavelength and an output of the excitation light α fluctuate. Therefore, an angle of the incident surface 21 is set such that the excitation light α is not incident on the incident surface 21 perpendicularly in a scanning range centered on an ideal resonance angle or enhancement angle.

Herein, the "resonance angle" means an incident angle when a light amount of the reflected light of the excitation light α emitted from the emitting surface 23 becomes minimum in a case of scanning the incident angle of the excitation light α with respect to the metal film 30. Also, the "enhancement angle" means the incident angle when a light amount of scattered light (hereinafter referred to as "plasmon scattered light") γ having the same wavelength as the excitation light α emitted above the measurement chip 10 is maximum in a case of scanning the incident angle of the excitation light α with respect to the metal film 30. In this embodiment, an angle between the incident surface 21 and the film depositing surface 22 and an angle between the film depositing surface 22 and the emitting surface 23 are both approximately 80 degrees.

Note that the resonance angle (and the reinforcement angle in the close vicinity thereof) is roughly determined by a design of the measurement chip 10. Design elements are a refractive index of the prism 20, a refractive index of the metal film 30, a thickness of the metal film 30, an extinction coefficient of the metal film 30, the wavelength of the excitation light α and the like. The resonance angle and the enhancement angle are shifted by the substance to be measured captured on the metal film 30, but an amount thereof is less than several degrees.

The prism 20 is formed of a dielectric material transparent to the excitation light α. The prism 20 has a birefringence characteristic more than little. Examples of materials of the prism 20 include resin and glass. Examples of the resin forming the prism 20 include polymethylmethacrylate (PMMA), polycarbonate (PC), and cycloolefin polymer. The material of the prism 20 is preferably resin having the refractive index of 1.4 to 1.6 and small birefringence.

Although it is described later in detail, in this embodiment, the metal film 30 provides a place where surface plasmon resonance occurs on a surface on the prism 20 side, and serves as a "reflecting unit" which reflects light which passes through a flow path 41 on a surface on the flow path 41 side.

The metal film 30 is arranged on the film depositing surface 22 of the prism 20. As a result, the surface plasmon resonance (hereinafter abbreviated as "SPR") occurs between photons of the excitation light α incident on the film depositing surface 22 under a total reflection condition and free electrons in the metal film 30, and it is possible to generate localized field light (generally also referred to as "evanescent light" or "near field light") on the surface of the metal film 30. The localized field light reaches a distance approximately the wavelength of the excitation light α from the surface of the metal film 30. The metal film 30 may be formed on an entire surface on the film depositing surface 22 or on a part of the film depositing surface 22. In this embodiment, the metal film 30 is formed on the entire surface of the film depositing surface 22.

The metal film 30 specularly reflects the light emitted from the light emitting unit 150 and passes through the flow path 41 so as to pass through the flow path 41 again. In this embodiment, the metal film 30 specularly reflects the first light $\delta_1$ entering the measurement chip 10 at the flow path lid 40 toward the flow path lid 40. Reflectivity of the metal film 30 is, for example, 40% to 98%. In addition, in a case where the metal film 30 is formed using silver, aluminum or the like as the material of the metal film 30, the metal film 30 having high reflectivity may be acquired. In this case, the reflectivity of the metal film 30 is, for example, 85% to 98%.

On the metal film 30, a capturing body for capturing the substance to be measured is immobilized. On the metal film 30, a region in which the capturing body is immobilized is especially referred to as a "reaction field". The capturing body may be immobilized on the entire surface of the metal film 30 or may be immobilized on a part of the surface. From a viewpoint of suppressing scattering of the first light $\delta_1$ by the capturing body, the capturing body is preferably not immobilized in a region serving as the reflecting unit (region in which the first light $\delta_1$ specularly reflects) of the metal film 30. Also, the capturing body specifically binds to the substance to be measured. Therefore, the substance to be measured may be immobilized on the metal film 30 via the capturing body.

A type of the capturing body is not especially limited as long as this may capture the substance to be measured. For example, the capturing body is an antibody (primary antibody) capable of specifically binding to the substance to be measured, a fragment thereof, an enzyme capable of specifically binding to the substance to be measured or the like.

The material of the metal film 30 is not especially limited as long as this may cause the surface plasmon resonance and specularly reflect the light on the surface thereof. Examples of the material of the metal film 30 include gold, silver, copper, aluminum, and alloys thereof. In this embodiment, the metal film 30 is a gold thin film. Although the thickness of the metal film 30 is not especially limited, this is preferably in a range of 20 nm to 60 nm from a viewpoint of efficiently causing SPR. A method of forming the metal film 30 is not especially limited. Examples of the method of forming the metal film 30 include sputtering, vapor deposition, and plating.

The flow path lid 40 is arranged on the metal film 30. In a case where the metal film 30 is formed only on a part of the film depositing surface 22 of the prism 20, the flow path lid 40 may also be arranged on the film depositing surface 22. In this embodiment, the flow path lid 40 is arranged on the metal film 30. By arranging the flow path lid 40 on the metal film 30, the flow path 41 which is a cavity for accommodating liquid is formed. In this embodiment, the flow path 41 includes a bottom surface, a top surface, and a pair of side surfaces connecting the bottom surface and the top surface. In this specification, a surface of the flow path 41 on the prism 20 side is referred to as the "bottom surface of the flow path 41", and a surface of the flow path 41 opposed to the bottom surface of the flow path 41 is referred to as the "top surface of the flow path 41". Also, an interval between the top surface of the flow path 41 and the bottom surface of the flow path 41 is set as a height h of the flow path 41.

As illustrated in FIG. 2, the flow path lid 40 includes a frame body 42, a liquid injecting unit covering film 43, and a liquid storage unit covering film 44. Two through holes are formed on the frame body 42. A concave portion (flow path groove) is formed on a rear surface of the frame body 42. The flow path lid 40 (frame body 42) is arranged on the metal film 30 (and the prism 20), and an opening of the concave portion is closed by the metal film 30, so that the flow path 41 is formed. Furthermore, an opening of one of the through holes is closed by the liquid injecting unit covering film 43, so that the liquid injecting unit 45 is formed, and an opening of the other through hole is closed by the liquid storage unit covering film 44, so that the liquid storage unit 46 is formed. The liquid storage unit covering film 44 is provided with a vent hole 47.

From a viewpoint of sufficiently securing the region where the localized field light reaches, it is preferable that the height h of the flow path 41 (depth of the flow path groove) is high to some extent. From a viewpoint of reducing an amount of impurities mixed in the flow path 41, it is preferable that the height h of the flow path 41 (depth of the flow path groove) is low. From this viewpoint, the height h of the flow path 41 is preferably in a range of 0.05 mm to 0.15 mm. Both ends of the flow path 41 are connected to the liquid injecting unit 45 and the liquid storage unit 46 formed on the flow path lid 40 so as to communicate the inside and the outside of the flow path 41 (refer to FIG. 2).

The frame body 42 is preferably formed of a material transparent to the light (fluorescence β and plasmon scattered light γ) emitted from an upper side of the metal film 30 and the first light $\delta_1$ (and the light δ' having the same wavelength as that of the first light $\delta_1$ (to be described later)) emitted toward the metal film 30. Examples of the material of the frame body 42 include glass and resin. Examples of the resin include polymethylmethacrylate resin (PMMA). Also, other portions of the frame body 42 may also be formed of an opaque material as long as this is transparent to the above-described light. The frame body 42 is joined to the metal film 30 or the prism 20 by, for example, bonding with a double-faced tape or an adhesive, laser welding, ultrasonic welding, crimping using a clamp member or the like.

The liquid injecting unit covering film 43 is a film in which a pipette chip 134 may be inserted capable of adhering closely to an outer periphery of the pipette chip 134 with no space when the pipette chip 134 is inserted. For example, the liquid injecting unit covering film 43 is a two-layer film of an elastic film and an adhesive film. The liquid injecting unit covering film 43 may also be provided with a fine through hole for inserting the pipette chip 134. In this embodiment, a pipette chip insertion through hole 48 having an outer diameter of 1.2 mm is provided on the liquid injecting unit covering film 43.

As described above, the liquid storage unit covering film 44 includes the vent holes 47. A configuration of the liquid storage unit covering film 44 is not especially limited. For example, the liquid storage unit covering film 44 may be a two-layer film similar to the liquid injecting unit covering film 43 described above.

As described above, in this embodiment, the measurement chip 10 and the liquid chip 50 are integrated (refer to FIG. 1). More specifically, the frame body 42 and the liquid chip 50 are integrated. The liquid chip 50 is a container for accommodating the liquid. The liquid chip 50 may also be used for accommodating a dispensed specimen or diluting the liquid to desired concentration. The liquid chip 50 includes a well for accommodating the liquid. An opening of the well may also be closed by a film or the like in a state of accommodating the liquid. The film closing the opening of the well may be removed by a user before use of the liquid chip 50. Also, in a case where the pipette chip 134 may penetrate the film, the liquid chip 50 may also be used in a state in which the opening of the well is closed by the film.

Examples of the liquid accommodated in the liquid chip 50 include the specimen containing the blood, a labeling solution containing the capturing body labeled with a fluorescent substance, a washing solution (buffering solution), liquid transparent to the first light $\delta_1$ (reference liquid to be described later, first liquid), a hemolytic agent, liquid containing a dye (second liquid to be described below), and diluted solutions thereof.

The measurement chip 10 and the liquid chip 50 are usually exchanged for each measurement. Also, the measurement chip 10 is preferably a structure a length of each piece of which is several millimeters to several centimeters, but this may also be a smaller structure or a larger structure not included in a category of "chip".

(SPFS Apparatus)

Next, each component of the SPFS apparatus 100 is described. As described above, the SPFS apparatus 100 includes the excitation light emitting unit 110, the signal detecting unit 120, the liquid sending unit 130, the transporting unit 140, the light emitting unit 150, the light detecting unit 160, and the control processing unit (processing unit) 170.

The excitation light emitting unit 110 emits the excitation light α (referred to as "eighth light" in claims). When detecting the fluorescence β, the excitation light emitting unit 110 emits a P wave to the metal film 30 toward the incident surface 21 so that the surface plasmon resonance occurs on the metal film 30. Herein, the "excitation light" is light which directly or indirectly excites the fluorescent substance. For example, the excitation light α is the light which allows the localized field light which excites the fluorescent substance to be generated on the surface of the metal film 30 when this is applied to the metal film 30 at an angle at which the surface plasmon resonance occurs via the prism 20. The excitation light emitting unit 110 includes a light source unit 111, an angle adjusting mechanism 112, and a light source control unit 113.

The first light source unit 111 emits light collimated and having constant wavelength and light amount so that a shape of an irradiation spot on the rear surface of the metal film 30 is substantially circular. The first light source unit 111 includes, for example, a light source, a beam shaping optical system, an APC mechanism, and a temperature adjusting mechanism (none of them is illustrated).

A type of the light source is not especially limited, and is, for example, the laser diode (LD). Other examples of the light source include laser light sources such as light emitting diodes and mercury lamps. The wavelength of the excitation light α emitted from the light source is, for example, in a range of 400 nm to 1000 nm. In a case where the excitation light α emitted from the light source is not a beam, the excitation light α is converted into the beam by a lens, a mirror, a slit or the like. Also, in a case where the excitation light α emitted from the light source is not monochromatic light, the excitation light α is converted into the monochromatic light by a diffraction grating or the like. Furthermore, in a case where the excitation light α emitted from the light source is not linear polarization, the excitation light α is converted into linear polarization light by a polarizer or the like.

The beam shaping optical system includes, for example, a collimator, a band pass filter, a linear polarization filter, a half wavelength plate, a slit, a zoom means and the like. The beam shaping optical system may include all of them or a part of them.

The collimator collimates the excitation light α emitted from the light source.

The band pass filter converts the excitation light α emitted from the light source into narrow band light having only a central wavelength. This is because the excitation light α emitted from the light source has a slight wavelength distribution width.

The linear polarization filter makes the excitation light α emitted from the light source the linear polarization light.

The half wavelength plate adjusts a polarization direction of the light so that the P wave component is incident on the metal film 30.

The slit and the zoom means adjust a beam diameter, a contour shape and the like of the excitation light α emitted from the light source so that the shape of the irradiation spot on the rear surface of the metal film 30 becomes a circle of a predetermined size.

The APC mechanism controls the light source so that an output of the light source is constant. More specifically, the APC mechanism detects an amount of light branched from the excitation light α with a photodiode not illustrated or the like. Then, the APC mechanism controls input energy by a recurrent circuit, thereby controlling the output of the light source to be constant.

The temperature adjusting mechanism is, for example, a heater, a Peltier element or the like. The wavelength and energy of the excitation light α emitted from the light source might fluctuate depending on the temperature. Therefore, by keeping the temperature of the light source constant by the temperature adjusting mechanism, the wavelength and energy of the excitation light α emitted from the light source are controlled to be constant.

The angle adjusting mechanism 112 adjusts the incident angle of the excitation light α with respect to the metal film 30 (interface between the prism 20 and the metal film 30 (film depositing surface 22)). In order to apply the light at a predetermined incident angle to a predetermined position of the metal film 30 via the prism 20, the angle adjusting mechanism 112 relatively rotates the optical axis of the excitation light α emitted from the light source and the chip holder 142. For example, the angle adjusting mechanism 112 rotates the light source unit 111 around an axis orthogonal to the optical axis of the excitation light α on the metal film 30 (axis perpendicular to the paper surface of FIG. 1). At that time, a position of a rotational axis is set such that the position of the irradiation spot on the metal film 30 scarcely changes even if the incident angle is scanned. Especially, displacement of the irradiation position may be minimized by setting the position of the rotational center in the vicinity of an intersection (between the irradiation position on the film depositing surface 22 and the incident surface 21) of the optical axes of the excitation light α emitted from the two light sources at both ends of a scanning range of the incident angle.

As described above, the angle at which the light amount of the plasmon scattered light γ becomes maximum out of the incident angle of the excitation light α emitted from the light source to the metal film 30 is the enhancement angle. By setting the incident angle of the excitation light α emitted from the light source to the enhancement angle or the angle in the vicinity thereof, high-intensity fluorescence β and plasmon scattered light γ may be detected. Although a basic incident condition of the excitation light α emitted from the light source is determined by the material and shape of the prism 20, the thickness of the metal film 30, the refractive index of the liquid in the flow path 41 and the like, an optimal incident condition slightly fluctuates depending on the type and amount of the capturing body in the flow path 41, a shape error of the prism 20 and the like. Therefore, it is preferable to acquire an optimum enhancement angle for each measurement.

The first light source control unit 113 controls various devices included in the first light source unit 111 to control the emission of the excitation light α from the first light source unit 111. The first light source control unit 113 is formed of, for example, a well-known computer or microcomputer including an arithmetic device, a control device, a storage device, an input device, and an output device.

The signal detecting unit 120 detects a signal (for example, fluorescence β, reflected light or plasmon scattered light γ) generated in the measurement chip 10 when the excitation light emitting unit 110 applies the excitation light α to the metal film 30 at the incident angle at which the surface plasmon resonance occurs via the prism 20 in a state in which the substance to be measured in the specimen is present on the metal film 30. The substance to be measured may be immobilized in the flow path 41 or not. In this embodiment, the signal detecting unit 120 detects the above-described signal in a state in which the substance to be measured contained in the specimen is immobilized on the metal film 30 and the specimen is not present in the flow path 41. The signal detecting unit 120 outputs a signal indicating a detected signal amount (for example, the light amount of the fluorescence β, the light amount of the reflected light δ' or the light amount of the plasmon scattered light γ) to the control processing unit 170. The signal detecting unit 120 includes a light receiving optical system unit 121, a position switching mechanism 122, and a first sensor control unit 127.

The light receiving optical system unit 121 is arranged on a normal line of the metal film 30 of the measurement chip 10. The light receiving optical system unit 121 includes a first lens 123, an optical filter 124, a second lens 125, and a first light receiving sensor 126.

The position switching mechanism 122 switches a position of the optical filter 124 on the optical path or out of the optical path in the light receiving optical system unit 121. Specifically, when the first light receiving sensor 126 detects the fluorescence β, the optical filter 124 is arranged on the optical path of the light receiving optical system unit 121, and when the first light receiving sensor 126 detects the plasmon scattered light γ, the optical filter 124 is arranged outside the optical path of the light receiving optical system unit 121.

The first lens 123 is, for example, a condensing lens, and condenses light (signal) emitted from the upper side of the metal film 30. The second lens 125 is, for example, an image forming lens, and forms an image of the light condensed by the first lens 123 on a light receiving surface of the first light receiving sensor 126. Between the two lenses, the light is a substantially parallel light flux.

The optical filter 124 is arranged between the first lens 123 and the second lens 125. When detecting fluorescence, the optical filter 124 transmits only the fluorescent component out of the light incident on the optical filter 124 and removes the excitation light component (plasmon scattered light γ). As a result, it is possible to guide only the fluorescent component to the first light receiving sensor 126 and detect the fluorescence β with a high S/N ratio. Examples of types of the optical filter 124 include an excitation light reflecting filter, a short wavelength cutting filter, and a band pass filter. Examples of the optical filter 124 include a filter including a multilayer film which reflects a predetermined light component and a color glass filter which absorbs a predetermined light component.

The first light receiving sensor 126 detects the fluorescence β and the plasmon scattered light γ. The first light receiving sensor 126 has high sensitivity capable of detecting weak fluorescence β from a minute amount of substance to be measured. The first light receiving sensor 126 is, for example, a photomultiplier tube (PMT), an avalanche photodiode (APD), a silicon photodiode (SiPD) or the like.

The first sensor control unit 127 controls detection of an output value of the first light receiving sensor 126, management of sensitivity of the first light receiving sensor 126 by the output value, change in the sensitivity of the first light receiving sensor 126 for acquiring an appropriate output value 126 and the like. The first sensor control unit 127 is formed of, for example, a well-known computer or microcomputer including an arithmetic device, a control device, a storage device, an input device, and an output device.

The liquid sending unit 130 supplies the liquid in the liquid chip 50 into the flow path 41 of the measurement chip 10 held by the chip holder 142. Also, the liquid sending unit 130 removes liquid from the flow path 41 of the measurement chip 10. Furthermore, the liquid sending unit 130 dispenses and dilutes the liquid in the liquid chip 50. The liquid sending unit 130 includes a pipette 131 and a pipette control unit 135.

The pipette 131 includes a syringe pump 132, a nozzle unit 133 connected to the syringe pump 132, and a pipette chip 134 attached to a tip end of the nozzle unit 133. Reciprocating motion of a plunger in the syringe pump 132 quantitatively sucks and discharges the liquid in the pipette chip 134.

The pipette control unit 135 includes a driving device of the syringe pump 132 and a moving device of the nozzle unit 133. The driving device of the syringe pump 132 is a device for reciprocating the plunger of the syringe pump 132 and includes, for example, a stepping motor. For example, the moving device of the nozzle unit 133 freely moves the nozzle unit 133 in a vertical direction. The moving device of the nozzle unit 133 is formed of, for example, a robot arm, a two-axis stage, or a vertically movable turntable.

The pipette control unit 135 drives the syringe pump 132 to suck various types of liquid from the liquid chip 50 into the pipette chip 134. Then, the pipette control unit 135 moves the nozzle unit 133 to insert the pipette chip 134 into the flow path 41 of the measurement chip 10, and drives the syringe pump 132 to inject the liquid in the pipette chip 134 into the flow path 41. Also, after introducing the liquid, the pipette control unit 135 drives the syringe pump 132 to suck the liquid in the flow path 41 into the pipette chip 134. By sequentially exchanging the liquid in the flow path 41 in this manner, the capturing body and the substance to be measured are allowed to react in the reaction field (primary reaction) and the substance to be measured and the capturing body labeled with the fluorescent substance are allowed to react (secondary reaction). Also, the liquid sending unit 130 sucks or discharges the liquid in the liquid chip 50 in the above-described manner, thereby dispensing or diluting the specimen.

The transporting unit 140 transports the measurement chip 10 to an installation position, a first measurement position for acquiring a measurement value indicating the amount of the substance to be measured in the specimen, a second measurement position for acquiring the hematocrit value, or a liquid sending position to immobilize. Herein, the "installation position" is a position for installing the measurement chip 10 in the SPFS apparatus 100. The "first measurement position" is a position at which the signal emitted from the measurement chip 10 is detected by the signal detecting unit 120 when the excitation light emitting unit 110 emits the excitation light α toward the measurement chip 10. The "second measurement position" is a position at which the light detecting unit 160 detects the light δ' reflected within the measurement chip 10 when the light emitting unit 150 emits the first light $\delta_1$ toward the metal film 30. Furthermore, the "liquid sending position" is a position at which the liquid sending unit 130 supplies the liquid into the flow path 41 of the measurement chip 10 or removes the liquid in the flow path 41 of the measurement chip 10.

The transporting unit 140 includes a transporting stage 141 and the chip holder 142.

The transporting stage 141 moves the chip holder 142 in one direction and in the opposite direction. The transporting stage 141 also has a shape which does not interfere with the optical paths of the light such as the excitation light α, the reflected light of the excitation light α, the fluorescence β, the plasmon scattered light γ, the first light $\delta_1$, and the reflected light δ' of the first light $\delta_1$. The transporting stage 141 is driven by, for example, a stepping motor or the like.

The chip holder 142 is fixed to the transporting stage 141 and detachably holds the measurement chip 10. The chip holder 142 has a shape capable of holding the measurement chip 10 which does not interfere with the optical path of the light such as the excitation light α, the reflected light of the excitation light α, the fluorescence β, the plasmon scattered light γ, the first light $\delta_1$, and the reflected light δ' of the first light $\delta_1$. For example, the chip holder 142 is provided with an opening through which the above-described light passes.

The light emitting unit 150 emits the first light $\delta_1$ including light of a wavelength absorbed by a red blood cell. In this embodiment, the light emitting unit 150 emits the first light $\delta_1$ from the flow path 41 side toward the metal film 30. It is preferable that the first light $\delta_1$ contains light of a wavelength absorbed by hemoglobin contained in the red blood cell. The light emitting unit 150 includes a second light source unit 151 and a second light source control unit 152.

The second light source unit 151 emits the first light $\delta_1$ which is collimated and has constant wavelength and light amount toward the metal film 30. The second light source unit 151 includes, for example, a light source, a collimator, an APC mechanism, and a temperature adjusting mechanism (none of them is illustrated). The collimator, the APC mechanism, and the temperature adjusting mechanism are similar to the collimator, the APC mechanism, and the temperature adjusting mechanism of the first light source unit 111, so that the description thereof is omitted. From a viewpoint of suppressing variation in wavelength of the first light $\delta_1$ due to temperature change of the light source, the second light source unit 151 preferably includes the temperature adjusting mechanism.

From a viewpoint of applying the first light $\delta_1$ to an inside of an outer edge of the metal film 30 and suppressing reduction in energy efficiency due to irradiation of the first light $\delta_1$ in a region other than the metal film 30, the light source is preferably the laser light source. The laser light source may irradiate the metal film 30 with the first light $\delta_1$ in a smaller irradiation spot as compared with that of a light source having low directivity such as an LED. The light source is, for example, a laser diode (LD). Other examples of the light source include laser light sources such as light emitting diodes and mercury lamps. The central wavelength of the first light $\delta_1$ from the light emitting unit 150 is, for example, 500 to 650 nm. In a case where the first light $\delta_1$ emitted from the light source is not a beam, the first light $\delta_1$ is converted into a beam by a lens, a mirror, a slit or the like.

The second light source control unit 152 controls various devices included in the second light source unit 151 and controls emission of the first light $\delta_1$ from the second light source unit 151. The second light source control unit 152 is formed of, for example, a well-known computer or microcomputer including an arithmetic device, a control device, a storage device, an input device, and an output device.

The light detecting unit 160 detects the light $\delta'$ acquired by the reflection of the first light $\delta_1$ in the measurement chip 10. For example, in a state in which the specimen is present in the flow path 41, the light detecting unit 160 detects second light $\delta_2$ acquired when the first light $\delta_1$ passes through the specimen in the flow path 41, is reflected by the metal film 30, and passes through again the specimen in the flow path 41 when the light emitting unit 150 emits the first light $\delta_1$ toward the metal film 30. The light detecting unit 160 outputs a signal indicating a light amount of the detected light $\delta'$. The light detecting unit 160 includes a second light receiving sensor 161 and a second sensor control unit 162.

The second light receiving sensor 161 detects the light $\delta'$ which is the first light $\delta_1$ reflected within the measurement chip 10. The second light receiving sensor 161 is, for example, a photomultiplier tube (PMT), an avalanche photodiode (APD), a silicon photodiode (SiPD) or the like.

The second sensor control unit 162 controls detection of an output value of the second light receiving sensor 161, management of sensitivity of the second light receiving sensor 161 by the output value, change in the sensitivity of the second light receiving sensor 161 for acquiring an appropriate output value and the like. The second sensor control unit 162 is formed of, for example, a well-known computer or microcomputer including an arithmetic device, a control device, a storage device, an input device, and an output device.

As described above, FIG. 2 is the schematic cross-sectional view illustrating the configuration of the hematocrit value acquiring unit in the measurement system 1 according to the first embodiment. FIG. 2 is a view as seen in a direction perpendicular to a plane (plane perpendicular to the paper surface of FIG. 1) including the optical axis of the first light $\delta_1$ and the optical axis of the reflected light $\delta'$ by the measurement chip 10 of the first light $\delta_1$. As illustrated in FIG. 2, the light emitting unit 150 (second light source unit 151) and the light detecting unit 160 (second light receiving sensor 161) are preferably arranged such that a plane including the optical axis of the first light $\delta_1$ and the optical axis of the reflected light $\delta'$ of the first light $\delta_1$ is in a longitudinal direction of the flow path 41. As a result, even if the position of the irradiation spot of the first light $\delta_1$ is displaced in the longitudinal direction of the flow path 41, it is possible to suppress the irradiation of the region other than the flow path 41 with the first light $\delta_1$. Also, in a case where the first light $\delta_1$ is obliquely incident on the metal film 30 as compared with a case where the first light $\delta_1$ is perpendicularly incident on the metal film 30, the shape of the irradiation spot of the first light $\delta_1$ on the metal film 30 extends in one direction. The direction in which the irradiation spot extends depending on the incident angle of the first light $\delta_1$ with respect to the metal film 30 is preferably in the longitudinal direction of the flow path 41. As a result, even if the position of the irradiation spot is displaced as compared with a case where the direction in which the irradiation spot extends is in a lateral direction of the flow path 41, the first light $\delta_1$ may be suppressed from being applied to the region other than the flow path 41 (metal film 30). Note that a cause of the positional displacement of the irradiation spot includes a positioning error of the chip holder 142 on the transporting stage 141, an installation error of the measurement chip 10 with respect to the chip holder 142 and the like.

The control processing unit 170 controls the angle adjusting mechanism 112, the first light source control unit 113, the position switching mechanism 122, the first sensor control unit 127, the pipette control unit 135, the transporting stage 141, the second light source control unit 152, and the second sensor control unit 162. The control processing unit 170 also serves as a processing unit which processes detection results of the signal detecting unit 120 (first light receiving sensor 126) and the light detecting unit 160 (second light receiving sensor 161). In this embodiment, the control processing unit 170 determines the measurement value indicating the amount of the substance to be measured in the specimen on the basis of the detection result of the fluorescence $\beta$ by the signal detecting unit 120. In addition, the control processing unit 170 determines the hematocrit value of the specimen on the basis of the detection result of the second light $\delta_2$ by the light detecting unit 160. Along with this, the control processing unit 170 corrects the above-described measurement value on the basis of the hematocrit value. As a result, the control processing unit 170 determines the amount (concentration) of the substance to be measured in plasma or serum. In addition, predetermined information (for example, various conversion coefficients and data regarding calibration curve) and the like used when processing the above-described detection results may also be recorded in the control processing unit 170 in advance. In this embodiment, a coefficient for converting a hematocrit related value (to be described later) to the hematocrit value is recorded in the control processing unit 170 in advance. The control processing unit 170 is formed of, for example, a well-known computer or microcomputer including an arithmetic device, a control device, a storage device, an input device, and an output device.

(Optical Path in SPFS Apparatus)

As illustrated in FIG. 1, the excitation light $\alpha$ enters the prism 20 from the incident surface 21. The excitation light $\alpha$ entering the prism 20 is incident on the metal film 30 at a total reflection angle (angle at which SPR occurs). In this manner, the localized field light may be generated on the metal film 30 by irradiating the metal film 30 with the excitation light $\alpha$ at an angle at which the SPR occurs. By this localized field light, the fluorescent substance which labels the substance to be measured present on the metal film 30 is excited and the fluorescence $\beta$ is released. The SPFS apparatus 100 detects the light amount (intensity) of the fluorescence $\beta$ emitted from the fluorescent substance. Note that although not especially illustrated, the reflected light of the excitation light α on the metal film 30 is emitted out of the prism 20 from the emitting surface 23.

Also, as illustrated in FIG. 2, in this embodiment, the first light $\delta_1$ enters the flow path 41 (measurement chip 10) via the frame body 42 of the flow path lid 40. The first light $\delta_1$ is reflected within the measurement chip 10 to become the light $\delta'$. The light $\delta'$ is emitted out of the flow path 41 (measurement chip 10) via the frame body 42 of the flow path lid 40. The SPFS apparatus 100 detects the light amount (intensity) of the light $\delta'$ emitted from the measurement chip 10.

In this specification, the reflected light $\delta'$ of the first light $\delta_1$ in the measurement chip 10 is assigned with different reference signs in accordance with a type of the liquid present in the flow path 41 or a reflection position in the measurement chip 10. When the specimen is present in the flow path 41, the first light $\delta_1$ passes through the specimen in the flow path 41, is reflected by the metal film 30, and passes through the specimen in the flow path 41 again to become the second light $\delta_2$. In a case where the flow path 41 is filled with the reference liquid transparent to the first light $\delta_1$, the first light $\delta_1$ passes through the reference liquid in the flow path 41, is reflected by the metal film 30, and passes through reference liquid in the flow path 41 again to become seventh light $\delta_7$.

(Operation Procedure of Measurement System)

Figure 3:
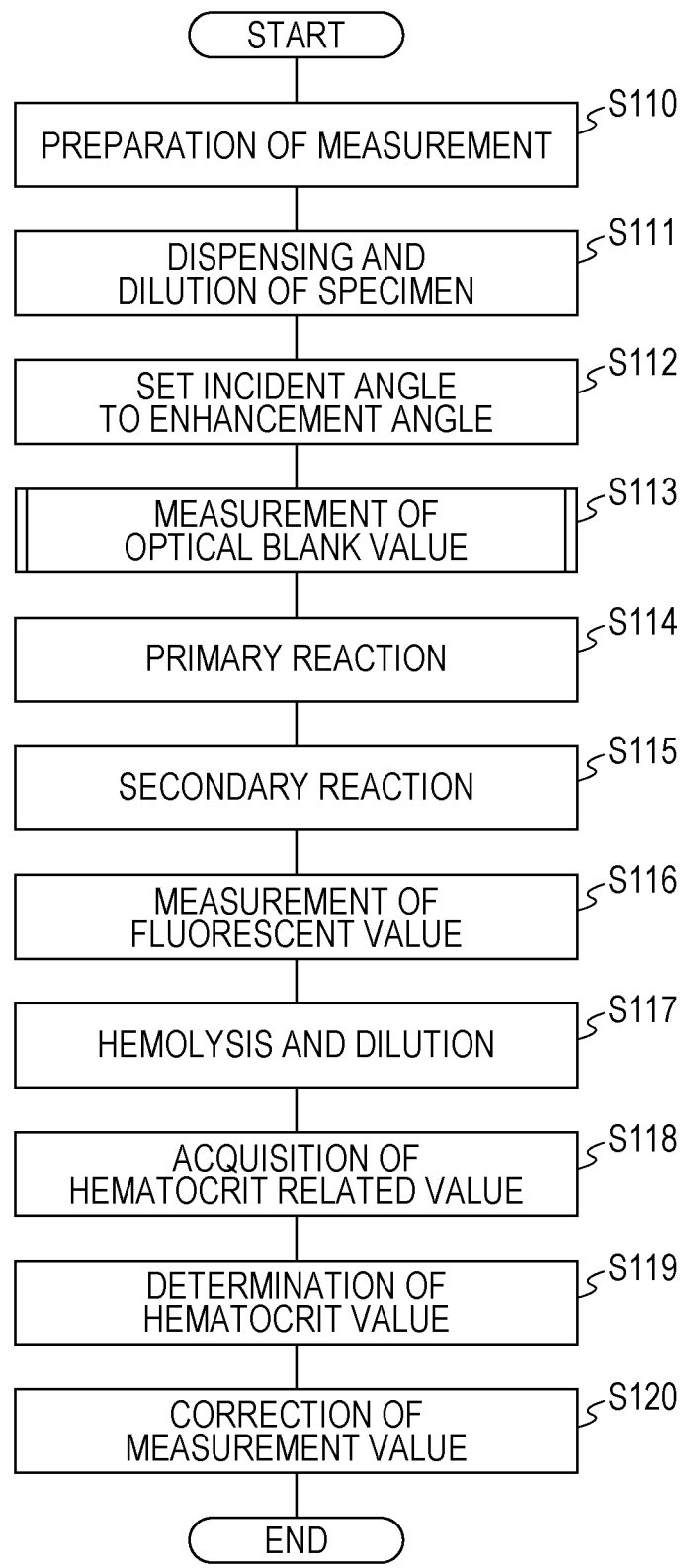
FIG. 3 is a flowchart illustrating an example of an operation procedure of the measurement system according to the first embodiment.
Figure 4:
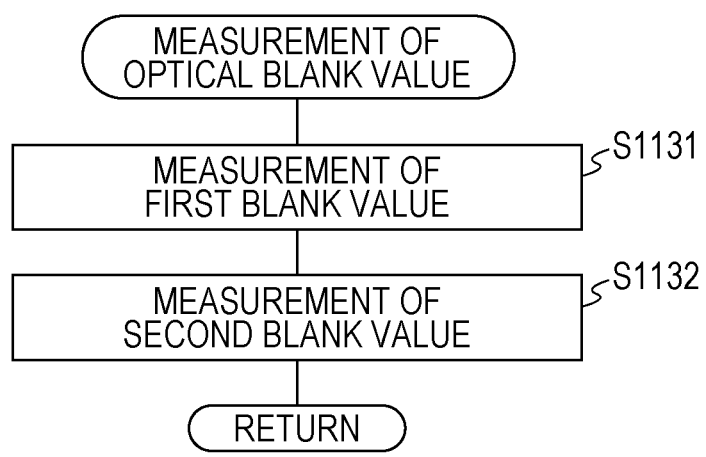
FIG. 4 is a flowchart illustrating steps in a measuring step of an optical blank value illustrated in FIG. 3.

Next, an operation procedure (measurement method according to the first embodiment) of the measurement system 1 according to the first embodiment is described. FIG. 3 is a flowchart illustrating an example of the operation procedure of the measurement system 1. FIG. 4 is a flowchart illustrating steps in a measuring step (step S113) of an optical blank value illustrated in FIG. 3. In this embodiment, a fluorescence value which is the light amount of the fluorescence β is measured as the measurement value indicating the amount of the substance to be measured in the specimen.

First, measurement is prepared (step S110). Specifically, the measurement chip 10 is installed in the chip holder 142 arranged at the installation position of the SPFS apparatus 100. In a case where a stored reagent is present on the metal film 30 of the measurement chip 10, the stored reagent is removed by washing the metal film 30 so that the capturing body may appropriately capture the substance to be measured.

Then, the specimen is dispensed and diluted (step S111). Specifically, the control processing unit 170 controls the pipette control unit 135 to divide the specimen in the liquid chip 50 into a first specimen for measuring the measurement value (fluorescence value) and a second specimen for measuring the hematocrit value. The first specimen and the second specimen are accommodated in empty wells of the liquid chip 50. At step S111, the first specimen is further diluted from a viewpoint of measurement accuracy and measurement sensitivity. Unless the first specimen is diluted, an amount of absorption (nonspecific adsorption) of impurities in the specimen to the capturing body increases and noise increases, and as a result, the measurement accuracy might be deteriorated. In addition, in a case where the amount of the substance to be measured is too large as compared with the amount of the capturing body, the amount of the substance to be measured which may be captured by the capturing body is saturated, and it becomes impossible to specify concentration of a highly concentrated specimen. As a diluent, for example, physiological saline may be used. The first specimen is, for example, diluted 2 to 50 times.

Next, the incident angle of the excitation light α with respect to the metal film 30 (film depositing surface 22) is set to the enhancement angle (step S112). Specifically, the control processing unit 170 controls the transporting stage 141 to move the measurement chip 10 from the installation position to the liquid sending position. The control processing unit 170 controls the pipette control unit 135 to provide the reference liquid (to be described later) transparent to the excitation light α in the liquid chip 50 into the flow path 41. The control processing unit 170 controls the transporting stage 141 to move the measurement chip 10 from the liquid sending position to the first measurement position. The control processing unit 170 controls the position switching mechanism 122 to move the optical filter 124 out of the optical path of the light receiving optical system unit 121. The control processing unit 170 controls the first light source control unit 113, the angle adjusting unit 112, and the first sensor control unit 127 so as to apply the excitation light α from the first light source unit 111 to a predetermined position of the metal film 30 while scanning the incident angle of the excitation light α with respect to the metal film 30 and detects the plasmon scattered light γ by the first light receiving sensor 126. As a result, the control processing unit 170 acquires data including a relationship between the incident angle of the excitation light α and the light amount of the plasmon scattered light γ. The acquired data is stored in the control processing unit 170. Then, the control processing unit 170 analyzes the data and determines the enhancement angle which is the incident angle at which the light amount of the plasmon scattered light γ becomes the maximum. Finally, the control processing unit 170 controls the angle adjusting unit 112 to set the incident angle of the excitation light α with respect to the metal film 30 (film depositing surface 22) to the determined enhancement angle.

Note that the enhancement angle is determined by the material and shape of the prism 20, the thickness of the metal film 30, the refractive index of the liquid in the flow path 41 and the like, but this slightly fluctuates by various causes such as the type and amount of the capturing body in the flow path 41, the shape error of the prism 20 and the like. Therefore, it is preferable to determine the enhancement angle each time the measurement is performed. The enhancement angle is determined on the order of approximately 0.1 degrees.

Next, the optical blank value is measured (step S113). In this embodiment, the optical blank value includes a first blank value used to determine the fluorescence value (measurement value) and a second blank value used to determine the hematocrit value. Herein, the "first blank value" means a light amount of background light emitted above the measurement chip 10 in a state in which the reference liquid is present in the flow path 41. Also, the "second blank value" means a light amount of the seventh light $\delta_7$ acquired when the first light $\delta_1$ passes through the reference liquid in the flow path 41, is reflected by the metal film 30, and passes through the reference liquid in the flow path 41 again when the light emitting unit 150 emits the first light $\delta_1$ toward the metal film 30 in the state in which the reference liquid is present in the flow path 41.

In this embodiment, the reference liquid is transparent to the excitation light α and the first light $\delta_1$. Note that a refractive index of the reference liquid is preferably the same as or equivalent to the refractive index of the specimen. As a result, it is possible to make the reflectivity of the first light $\delta_1$ on a bottom surface of the flow path groove (concave portion) of the frame body 42 (top surface of the flow path 41) the same or equivalent and to make the reflectivity of the light δ on the surface of the metal film 30 the same or equivalent between a case where the reference liquid is present in the flow path 41 and a case where the specimen is present in the flow path 41.

As illustrated in FIG. 4, at step S113, the first blank value is first measured (step S1131). The control processing unit 170 controls the position switching mechanism 122 to move the optical filter 124 on the optical path of the light receiving optical system unit 121. Next, the control processing unit 170 controls the first light source control unit 113 to emit the excitation light α from the first light source unit 111 toward the metal film 30 (film depositing surface 22). At the same time, the control processing unit 170 controls the first sensor control unit 127 to detect a light amount of light having substantially the same wavelength as that of the fluorescence β by the first light receiving sensor 126. As a result, the first light receiving sensor 126 may measure the light amount (first blank value) of light which becomes noise in the measurement of the fluorescence value (step S116). The first blank value is transmitted to the control processing unit 170 and recorded.

Then, the second blank value is measured (step S1132). The control processing unit 170 controls the transporting stage 141 to move the measurement chip 10 from the first measurement position to the second measurement position. Then, the control processing unit 170 controls the second light source control unit 152 to allow the second light source unit 151 to apply the first light $δ_1$ to the metal film 30. At the same time, the control processing unit 170 controls the second sensor control unit 162 to detect the seventh light $δ_7$ reflected by the metal film 30 by the second light receiving sensor 161. As a result, the second light receiving sensor 161 may measure a light amount (second blank value) of light which becomes noise in the measurement of the hematocrit value. The second blank value is transmitted to the control processing unit 170 and recorded. Note that the second blank value may also be recorded as an absorbance $OD_1$ of the reference liquid represented by following equation (1).

[Equation 1]

$$OD_1 = -\log\frac{I_1}{I_0} \quad (1)$$

[In equation (1) above, $OD_1$ represents the absorbance of the reference liquid, $I_0$ represents the light amount of the first light $δ_1$, and $I_1$ represents the light amount of the seventh light $δ_7$.]

Next, the substance to be measured in the specimen and the capturing body on the metal film 30 are allowed to react with each other (primary reaction; step S114). Specifically, the control processing unit 170 controls the transporting stage 141 to move the measurement chip 10 from the second measurement position to the liquid sending position. Thereafter, the control processing unit 170 controls the pipette control unit 135 to discharge the reference liquid in the flow path 41 and provides the first specimen diluted at step S111 into the flow path 41. As a result, in a case where the substance to be measured is present in the specimen, at least a part of the substance to be measured is captured by the capturing body on the metal film 30. Note that the first specimen is not hemolyzed. Thereafter, the interior of the flow path 41 is washed with the buffering solution or the like to remove the substance not captured by the capturing body.

Note that examples of the substance to be measured include troponin, myoglobin, and creatine kinase-MB (CK-MB).

Subsequently, the substance to be measured captured by the capturing body on the reflecting film 30 is labeled with the fluorescent substance (secondary reaction; step S115). Specifically, the control processing unit 170 controls the pipette control unit 135 to provide the fluorescent labeling solution in the liquid chip 50 into the flow path 41. As a result, the substance to be measured may be labeled with the fluorescent substance. The fluorescent labeling solution is, for example, the buffering solution containing an antibody (secondary antibody) labeled with the fluorescent substance. Thereafter, the interior of the flow path 41 is washed with the buffering solution or the like to remove a free fluorescent substance and the like.

Next, the fluorescence β released from the fluorescent substance labeling the substance to be measured in the reaction field is detected and the fluorescence value is measured (step S116). Specifically, the control processing unit 170 controls the pipette control unit 135 to provide the buffering solution for measurement in the liquid chip 50 into the flow path 41. The control processing unit 170 controls the transporting stage 141 to move the measurement chip 10 from the liquid sending position to the first measurement position. Thereafter, the control processing unit 170 controls the first light source control unit 113 to apply the excitation light α from the first light source unit 111 of the excitation light emitting unit 110 to the rear surface of the metal film 30 corresponding to the region in which the capturing body is immobilized via the prism 20 at the incident angle at which the surface plasmon resonance occurs in a state in which the substance to be measured contained in the specimen is immobilized and the specimen is not present. At the same time, the control processing unit 170 controls the first sensor control unit 127 to detect the fluorescence β (signal) generated in the measurement chip 10 by the first light receiving sensor 126. As a result, the first light receiving sensor 126 acquires the fluorescence value (measurement value) which is the light amount of the fluorescence β. The fluorescence value is transmitted to the control processing unit 170 and recorded. Note that, in this specification, the "state in which no specimen is present" means a state in which operation of removing the specimen from the flow path 41 is performed. That is, it suffices that there is substantially no specimen in the flow path 41, and a small amount of specimen which cannot be removed may be left in the flow path 41.

Next, blood in the second specimen dispensed at step S111 is hemolyzed and diluted (step S117). The control processing unit 170 controls the pipette control unit 135 to provide a hemolytic agent accommodated in another liquid chip 50 into the second specimen accommodated in the liquid chip 50. As a result, the blood in the second specimen may be hemolyzed and diluted. At that time, the second specimen is diluted, for example, 1 to 20 times. At that time, when a dilution ratio of the second specimen is one, this means that the second specimen is not diluted. The larger the dilution ratio, the smaller the amount of light absorbed by the specimen. Therefore, when the dilution ratio is too large, sufficient measurement resolution cannot be acquired.

Next, the hematocrit related value is acquired (step S118). Specifically, the control processing unit 170 controls the transporting stage 141 to move the measurement chip 10 from the first measurement position to the liquid sending position. The control processing unit 170 controls the pipette control unit 135 to provide the specimen in the state in which the blood is hemolyzed in the liquid chip 50 into the flow path 41. Next, the control processing unit 170 controls the transporting stage 141 to move the measurement chip 10 from the liquid sending position to the second measurement position. Next, in the state in which the specimen is present in the flow path 41, the control processing unit 170 controls the second light source control unit 152 of the light emitting unit 150 to allow the second light source unit 151 to apply the first light $\delta_1$ to the metal film 30. At the same time, the control processing unit 170 controls the second sensor control unit 162 to detect the second light $\delta_2$ which passes through the specimen in the flow path 41, is reflected by the metal film 30, and passes through the specimen in the flow path 41 again by the second light receiving sensor 161. As a result, the second light receiving sensor 161 measures the light amount of the second light $\delta_2$. The measurement value is transmitted to the control processing unit 170 and recorded. Note that the light amount of the second light $\delta_2$ may also be recorded as an absorbance $OD_2$ of the specimen represented by following equation (2).

[Equation 2]

$$OD_2 = -\log\frac{I_2}{I_0} \quad (2)$$

[In equation (2) described above, $OD_2$ represents the absorbance of the specimen, $I_0$ represents the light amount of the first light $\delta_1$, and $I_2$ represents the light amount of the second light $\delta_2$.]

The absorbance $OD_2$ of the specimen includes a signal component caused by the absorption of the light by the specimen and the noise component (second blank value) caused by other factors. Therefore, the control processing unit 170 may calculate the signal component by subtracting the noise component (second blank value) acquired at step S1132 from the absorbance $OD_2$ of the specimen acquired at step S118. The control processing unit 170 calculates a hematocrit related value Hct' represented by equation (3) below on the basis of the measurement value (light amount of the second light $\delta_2$ or the absorbance $OD_2$ of the specimen) acquired at step S118 and the measurement value acquired at step S1132 (light amount of the seventh light $\delta_7$ or the absorbance $OD_1$ of the reference liquid).

[Equation 3]

$$Hct' = -\log\frac{I_2}{I_1} \quad (3)$$

[In equation (3) described above, Hct' represents the hematocrit related value, $I_1$ represents the light amount of the seventh light $\alpha_7$, and $I_2$ represents the light amount of the second light $\delta_2$.]

Note that the absorbance of the specimen (hemoglobin) varies according to the wavelength of the first light $\delta_1$. From a viewpoint of stabilizing the wavelength of the first light $\delta_1$ and measuring the absorbance with a high degree of accuracy, it is preferable to adjust the temperature of the light source of the light emitting unit 150 to be kept constant.

Next, the hematocrit value is determined (step S119). The control processing unit 170 determines the hematocrit value of the specimen on the basis of the detection result of the second light $\delta_2$ by the light detecting unit 160. In this embodiment, the control processing unit 170 calculates a hematocrit value Hct by multiplying the hematocrit related value acquired at step S118 by a correction coefficient recorded in the control processing unit 170 in advance.

Note that, as described above, the absorbance varies according to the wavelength of the first light $\delta_1$ emitted from the light emitting unit 150. Therefore, from a viewpoint of acquiring a more accurate hematocrit value, it is preferable to correct the hematocrit value on the basis of the wavelength of the first light $\delta_1$. Consider, for example, a case where the hematocrit value is calculated with a reference value of the wavelength of the first light $\delta_1$ set to 520 nm. In this case, when the wavelength of the second light $\delta_2$ detected by the light detecting unit 160 is 530 nm, the hematocrit value Hct may be corrected so as to be the value when the wavelength of the first light $\delta_1$ is 520 nm in consideration of a shift amount of an absorption rate (absorption amount) of the red blood cell corresponding to a shift amount (10 nm) between the measurement value and the reference value.

Finally, the measurement value is corrected on the basis of the hematocrit value (step S120). The fluorescence value contains the fluorescent component (signal component) derived from the fluorescent substance which labels the substance to be measured and the noise component (first blank value) caused by the factors other than the fluorescent substance. Therefore, the control processing unit 170 may calculate the measurement value (signal component) indicating the amount of the substance to be measured in the specimen by subtracting the first blank value acquired at step S1131 from the fluorescence value acquired at step S116. Furthermore, the control processing unit 170 converts the calculated measurement value into the amount of the substance to be measured in the plasma by multiplying the calculated measurement value by a conversion coefficient c expressed by following equation (4).

[Equation 4]

$$c = \frac{df(1 - Hct)}{df - 1 + (1 - Hct)} \quad (4)$$

[In equation (4) described above, Hct represents the hematocrit value (0 to 100%), and df represents the dilution ratio of the diluent.]

By the above-described procedure, the amount of the substance to be measured in the plasma may be determined.

Note that, from a viewpoint of measuring the hematocrit value with a high degree of accuracy, the measurement of the second blank value (step S1132) may also be performed after the measurement of the fluorescence value (step S116). This may shorten a time interval between the measurement of the second blank value (step S1132) and the acquisition of the hematocrit related value (step S118), thereby making an effect of variation in power of the light source of the light emitting unit 150, variation in wavelength of the first light $\delta_1$ caused by change in temperature of the light emitting unit 150 and the like small. Furthermore, it is also conceivable that a scattering state of the first light $\delta_1$ on the surface of the metal film 30 changes due to the primary reaction and the secondary reaction, but by measuring the second blank value (step S1132) and acquiring the hematocrit related value (step S118) after the first reaction and the second reaction, there is no effect of the change in the scattering state described above. From this viewpoint, it is preferable to measure the second blank value (step S1132) after the measurement of the fluorescence value (step S116).

Also, a mode in which the step of setting the incident angle to the enhancement angle (step S112), the step of measuring the optical blank value (step S113), and the step of performing the primary reaction (step S114) are performed in this order is described. However, the measurement method and the measurement apparatus according to the present invention are not limited to this order. For example, the incident angle may be set to the enhancement angle after the primary reaction is performed, or the primary reaction may be performed after measuring the optical blank value.

Also, after the step of performing the primary reaction (step S114), the step of performing the secondary reaction (step S115) is performed (two-step method). However, a timing of labeling the substance to be measured with the fluorescent substance is not especially limited. For example, before introducing a specimen solution into the flow path 41 of the measurement chip 10, the labeling solution may be added to the specimen solution to label the substance to be measured with the fluorescent substance in advance. Alternatively, the specimen solution and the labeling solution may also be simultaneously injected into the flow path of the measurement chip 10. In the former case, the substance to be measured labeled with the fluorescent substance is captured by the capturing body by injecting the specimen solution into the flow path 41 of the measurement chip 10. In the latter case, the substance to be measured is labeled with the fluorescent substance and the substance to be measured is captured by the capturing body. In either case, both the primary reaction and the secondary reaction may be completed by introducing the specimen solution into the flow path 41 of the measurement chip 10 (one-step method).

(Effect)

In this embodiment, the flow path 41 for accommodating the liquid is a cavity. Therefore, in the measurement method according to this embodiment, light scattering by test paper does not occur as in the conventional measurement method in which optical measurement is performed in a state in which the specimen is absorbed by the test paper. Also, in the measurement method according to this embodiment, light absorption by a dye does not occur as in the conventional measurement method using a coloring reaction with the dye. As a result, in the measurement method of this embodiment, the hematocrit value of the specimen may be measured with a high degree accuracy, and the amount of the substance to be measured in the plasma may be determined with a high degree of accuracy.

Also, in the measurement method according to this embodiment, the light which becomes the second light $\delta_2$ is allowed to reciprocate within the flow path 41 by the metal film 30. This makes it possible to increase the optical path length of the light which becomes the second light $\delta_2$ in the flow path 41 as compared with a case where the reflection by the metal film 30 is not utilized. As a result, it is possible to measure the hematocrit value with a high degree of accuracy by increasing the amount of light absorbed by the specimen. As a result, the amount of the substance to be measured in the plasma may be determined with a high degree of accuracy. In addition, although the optical path length of the light in the specimen fluctuates due to scattering by the test paper in the conventional measurement method, the flow path 41 has a shape of a constant cavity, so that the optical path length of the light in the specimen is stabilized in the measurement method according to this embodiment. From this point of view as well, the hematocrit value may be measured with a high degree of accuracy, and the amount of the substance to be measured in the plasma may be determined with a high degree of accuracy.

Also, in the measurement method according to this embodiment, the measurement value (fluorescence value) indicating the amount of the substance to be measured contained in the specimen is acquired by using the SPFS. When the excitation light $\alpha$ is applied to the metal film 30 so as to generate the SPR, the localized field light only reaches a region apart from the surface of the metal film 30 by approximately the wavelength of the excitation light $\alpha$. That is, from a viewpoint of measuring the fluorescence value, necessity of increasing the height of the flow path 41 beyond the region is small. On the other hand, by increasing the height of the flow path 41, the amount of impurities which might be mixed into the flow path 41 increases, so that the measurement accuracy of the fluorescence value might be reduced. From such a viewpoint, the height of the flow path 41 is preferably low. However, when the height of the flow path 41 is low, the optical path length of the light in the flow path 41 also becomes short, so that the amount of light absorbed by the specimen decreases, and it is conceivable that the hematocrit value cannot be measured with a high degree of accuracy. Therefore, from a viewpoint of measuring the hematocrit value with a high degree of accuracy while sufficiently securing the amount of light absorbed by the specimen, the height of the flow path 41 is preferably high. Regarding this point, in the measurement method according to this embodiment, although the height of the flow path 41 is low, the optical path length of the light in the specimen is increased by providing the metal film 30. Therefore, it is possible to secure the amount of light absorbed by the specimen while suppressing the amount of impurities which might be mixed in the flow path 41. As a result, both the fluorescence value and the hematocrit value may be measured with a high degree of accuracy.

In the measurement method according to this embodiment, the second blank value may be measured at step S1132, and the effect of the noise component may be removed (step S118). Therefore, it is possible to measure the hematocrit value with a higher degree of accuracy.

Furthermore, in the above-described embodiment, the second blank value is measured (step S1132) before the primary reaction (step S114). Therefore, even if the washing in the flow path 41 after the primary reaction is not sufficient and the blood remains in the flow path 41, the measurement of the second blank value is not affected by residual blood, so that the hematocrit value may be measured with a high degree of accuracy. From this point of view, it is preferable to measure the second blank value (step S1132) before the primary reaction (step S114).

Furthermore, in this embodiment, the hematocrit value is determined on the basis of the detection result of the second light $\delta_2$ which passes through the specimen in a state in which the blood is hemolyzed. Hemolysis of blood makes it possible to reduce the effect of light scattering due to the red blood cell. As a result, the hematocrit value may be measured with a higher degree of accuracy, and the amount of the substance to be measured in the plasma may be determined with a higher degree of accuracy. On the other hand, the first specimen used for measuring the fluorescence value does not cause hemolysis of the blood. As a result, it is possible to prevent protease (proteolytic enzyme) in the red blood cell from flowing out of the red blood cell by hemolysis to decompose the substance to be measured, and the fluorescence value may be measured with a higher degree of accuracy.

Second Embodiment

In a second embodiment, a hematocrit value is corrected on the basis of a height of a flow path. Since a configuration of a measurement system and a measurement apparatus according to the second embodiment is the same as that of the measurement system and measurement apparatus according to the first embodiment except a light detecting unit, the same reference sign is assigned to the same component and the description thereof is omitted.

(Measurement System and SPFS Apparatus)

FIG. 1 is a schematic diagram illustrating a configuration of a measurement system 2 according to the second embodiment. As illustrated in FIG. 1, the measurement system 2 includes a measurement chip 10 and an SPFS apparatus 200. The SPFS apparatus 200 includes an excitation light emitting unit 110, a signal detecting unit 120, a liquid sending unit 130, a transporting unit 140, a light emitting unit 150, a light detecting unit 260, and a control processing unit (processing unit) 270. In the second embodiment, the light emitting unit 150 and the light detecting unit 260 form a hematocrit value acquiring unit for acquiring a hematocrit value of a specimen.

The light detecting unit 260 detects light δ' which is reflected light of first light $δ_1$ in the measurement chip 10. The light detecting unit 260 outputs a signal indicating a light amount of the detected light δ'. The light detecting unit 260 includes a second light receiving sensor 261 and a second sensor control unit 162.

The second light receiving sensor 261 is an array sensor for receiving the light δ' which is the reflected light of the first light $δ_1$ in the measurement chip 10. An example of a type of the second light receiving sensor 261 is a one-dimensional imaging element (line sensor) or a two-dimensional imaging element (image sensor). Examples of the second light receiving sensor 261 include a charge coupled device (CCD) and a complementary metal-oxide semiconductor device (CMOS).

The control processing unit 270 is similar to the control processing unit 170 according to the first embodiment except that control for measuring the height of a flow path 41 is added, so that the description thereof is omitted.

(Operation Procedure of Measurement System)

Figure 5:
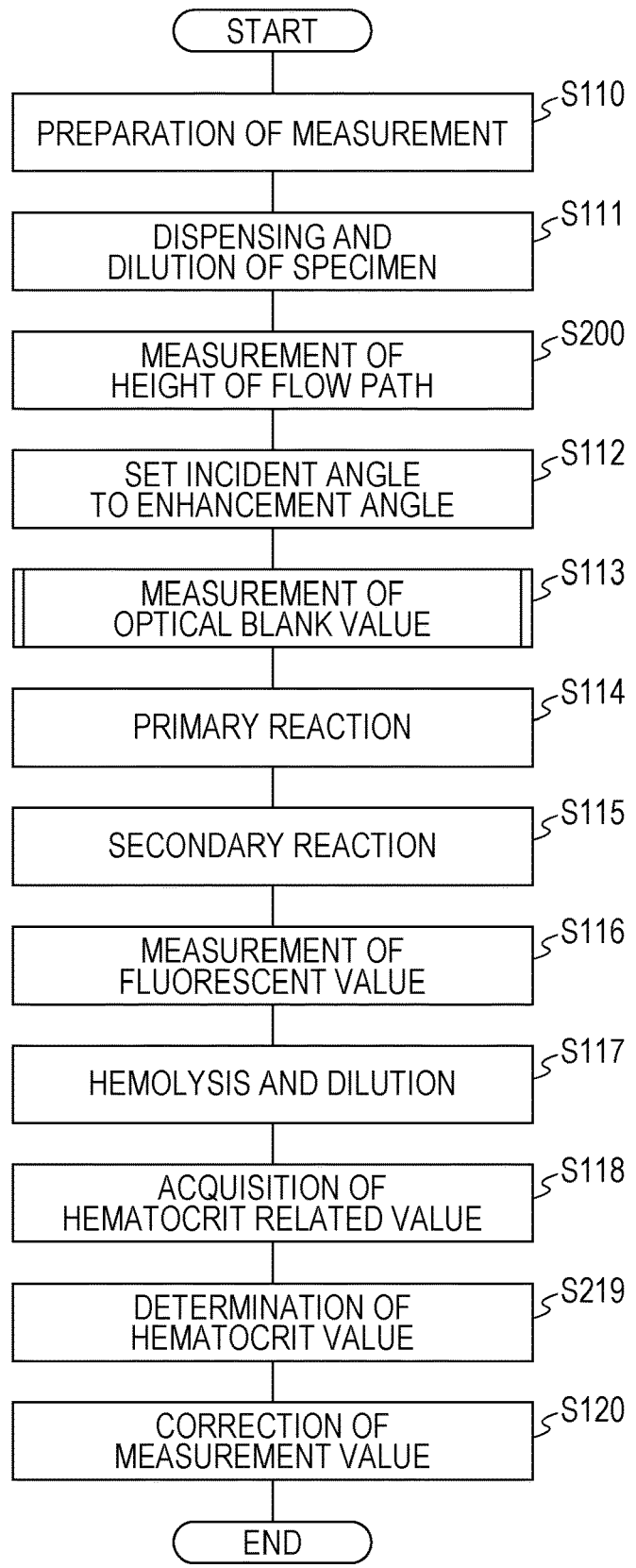
FIG. 5 is a flowchart illustrating an example of an operation procedure of the measurement system according to the second embodiment.

Next, an operation procedure (measurement method according to the second embodiment) of the measurement system 2 according to the second embodiment is described. FIG. 5 is a flowchart illustrating an example of the operation procedure of the measurement system 2.

In a manner similar to the measurement method according to the first embodiment, steps from preparing measurement (step S110) to dispensing and diluting the specimen (step S111) are performed.

Next, the height of the flow path 41 is measured (step S200). Specifically, the control processing unit 270 controls a transporting stage 141 to move the measurement chip 10 from an installation position to a second measurement position. Thereafter, the control processing unit 270 controls a second light source control unit 152 to allow a second light source unit 151 to emit the first light $δ_1$ toward a metal film 30. At the same time, the control processing unit 270 controls the second sensor control unit 162 to detect third light $δ_3$ acquired when the first light $δ_1$ passes through the flow path 41, is reflected by the metal film 30, and passes through the flow path 41 again, fourth light $δ_4$ acquired when the first light $δ_1$ is reflected by a surface opposed to the metal film 30 of the flow path 41 (top surface of the flow path 41), and ninth light $δ_9$ acquired when the first light $δ_1$ is reflected by a top surface of a frame body 42 by the second light receiving sensor (array sensor) 261 in a distinguishing manner in a first state in which the flow path 41 is a cavity. A detection result of the third light $δ_3$ and a detection result of the fourth light $δ_4$ are transmitted to the control processing unit 270 and recorded.

Next, the control processing unit 270 controls the transporting stage 141 to move the measurement chip 10 from the second measurement position to a liquid sending position. The control processing unit 270 controls a pipette control unit 135 to provide first liquid transparent to the first light $δ_1$ accommodated in a liquid chip 50. A refractive index of the first liquid is larger than a refractive index of air (1.0) and preferably closer to a refractive index (1.5) of a flow path lid 40 (frame body 42). The control processing unit 270 controls the transporting stage 141 to move the measurement chip 10 from the liquid sending position to the second measurement position again. Next, the control processing unit 270 allows the second light source unit 151 to apply the first light $δ_1$ to the metal film 30. At the same time, the control processing unit 270 controls the second sensor control unit 162 to detect fifth light $δ_5$ acquired when the first light $δ_1$ passes through the first liquid in the flow path 41, is reflected by the metal film 30, and passes through the first liquid in the flow path 41 again and ninth light $δ_9$ acquired when the first light $δ_1$ is reflected by the top surface of the frame body 42 in a second state in which the flow path 41 is filled with the first liquid by the second light receiving sensor (array sensor) 261. A detection result of the fifth light $δ_5$ is transmitted to the control processing unit 270 and recorded.

Figure 6A:
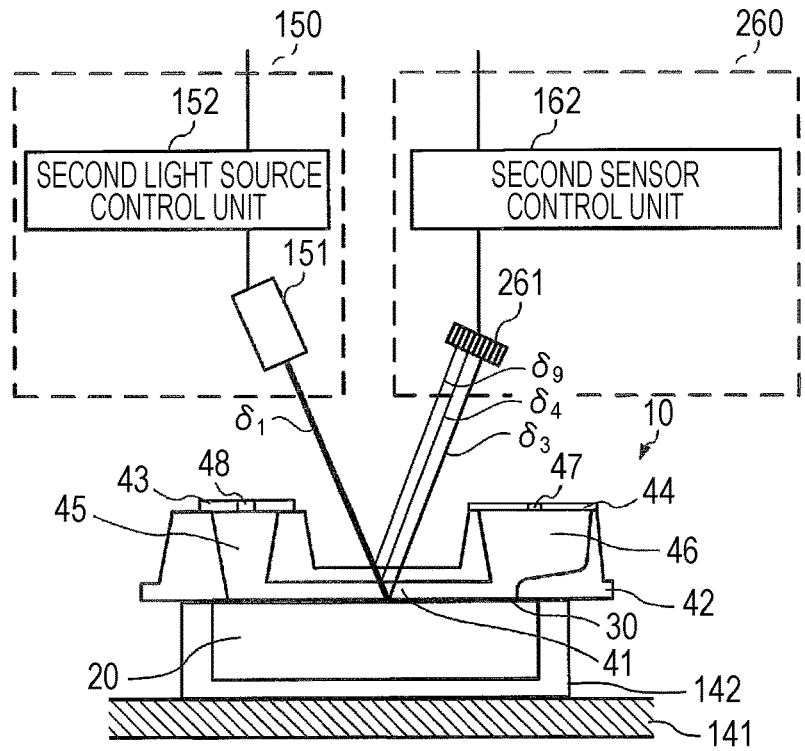
FIGS. 6A and 6B are views for illustrating measurement of a height of a flow path in the measurement system according to the second embodiment and are schematic cross-sectional views illustrating a configuration of a hematocrit value acquiring unit in the measurement system according to the second embodiment.
Figure 6B:
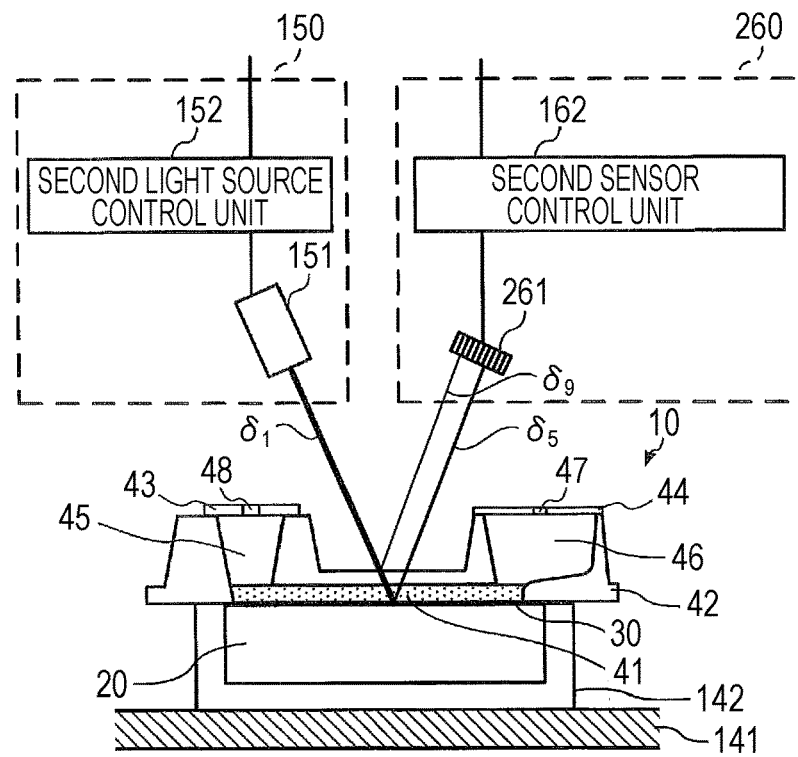

FIGS. 6A and 6B are views for illustrating measurement of the height of the flow path 41 and are schematic diagrams illustrating a configuration of the hematocrit value acquiring unit in the measurement system 2 according to the second embodiment. In FIGS. 6A and 6B, in order to illustrate an optical path in the measurement chip 10, a cross-section of the measurement chip 10 is not hatched. Note that FIG. 6A illustrates a state (first state) in which the flow path 41 is the cavity, and FIG. 6B illustrates a state (second state) in which the flow path 41 is filled with the first liquid.

First, the detection of the third light $δ_3$, the fourth light $δ_4$, and the ninth light $δ_9$ in the first state is described. As illustrated in FIG. 6A, the first light $δ_1$ emitted from the second light source unit 151 is reflected not only by a surface of the metal film 30 (bottom surface of the flow path 41) but also by the top surface of the frame body 42 and a bottom surface of a concave portion of the frame body 42 (top surface of the flow path 41). The light δ' (third light $δ_3$, fourth light $δ_4$, and ninth light $δ_9$) reflected at different positions reaches different positions of the second light receiving sensor 261. The ninth light $δ_9$, the fourth light $δ_4$, and the third light $δ_3$ reach a light receiving surface of the second light receiving sensor 261 (array sensor) at a position away from the light emitting unit 150 in this order. In this manner, the second light receiving sensor 261 may measure light amounts of the light of different reflection positions in the measurement chip 10 in a distinguishing manner.

Next, the detection of the fifth light $δ_5$ and the ninth light $δ_9$ in the second state is described. As illustrated in FIG. 6B, the first light $δ_1$ emitted from the second light source unit 151 is reflected not only by the surface of the metal film 30 (bottom surface of the flow path 41) but also by the top surface of the frame body 42. In the second state, as compared with the case of the first state, the light is not reflected by the bottom surface of the concave portion of the frame body 42 (top surface of the flow path 41). This is because the flow path 41 is filled with the first liquid having the refractive index equivalent to the refractive index of the frame body 42.

Then, the height of the flow path 41 is determined on the basis of the detection results of the third light $\delta_3$, the fourth light $\delta_4$, and the ninth light $\delta_9$ in the first state and the detection results of the fifth light $\delta_5$ and the ninth light $\delta_9$ in the second state. For example, suppose that data illustrated in following table 1 is acquired on the basis of the detection result in the first state and the detection result in the second state. Table 1 illustrates a reflection position number, reflectivity at each reflection position, a difference between the result in the first state and the result acquired in the second state (reflectivity).

TABLE 1

| Reflection Position No. | Reflectivity [%] | | |
| --- | --- | --- | --- |
| | First State | Second State | Difference |
| 1 | 4 | 4 | 0 |
| 2 | 4 | 0 | 4 |
| 3 | 60 | 60 | 0 |

In the first state and the second state, the reflectivity at a reflection position 1 was the same, which was 4%. Also, the reflectivity at a reflection position 3 was the same in the first state and the second state, which was 60%. On the other hand, the reflectivity at a reflection position 2 in the first state and the reflectivity at the reflection position 2 in the second state were different from each other.

The reflectivity at the bottom surface of the flow path 41 is larger than the reflectivity at a position other than the bottom surface of the flow path 41. That is, the reflection position 3 of larger reflectivity may be determined to be the bottom surface of the flow path 41. In this manner, the position of the bottom surface of the flow path 41 might be detected with a high degree of accuracy.

On the other hand, the reflectivity at the top surface of the flow path 41 and the reflectivity at the top surface of the frame body 42 are comparable with each other and small. Therefore, the position of the top surface of the flow path 41 and the position of the top surface of the frame body 42 are less easily detected with a high degree of accuracy. Therefore, the control processing unit 270 acquires a difference between the detection result in the first state and the detection result in the second state, thereby extracting only a peak of the fourth light $\delta_4$ reflected at the reflection position 2 to determine the reflection position 2. As described above, the reflection position 2 at which the reflectivity changes between the first state and the second state may be determined as the top surface of the flow path 41.

Once the reflection position 2 is determined, the remaining reflection position 1 may also be determined. The reflection position 1 at which the reflectivity does not change between the first state and the second state may be determined to be the top surface of the frame body 42.

Therefore, the control processing unit 270 may determine the height of the flow path 41 on the basis of the position of the bottom surface of the flow path 41 and the position of the top surface of the flow path 41.

Then, in a manner similar to the measurement method according to the first embodiment, steps from setting an incident angle to an enhancement angle (step S112) to acquiring a hematocrit related value (step S118) are performed.

Next, the hematocrit value is determined (step S219). The control processing unit 270 determines the hematocrit value of the specimen on the basis of the detection result of the second light $\delta_2$ by a light detecting unit 160. In this embodiment, the control processing unit 270 calculates the hematocrit value by multiplying the hematocrit related value acquired at step S118 by a correction coefficient recorded in the control processing unit 270 in advance. Furthermore, in this embodiment, the hematocrit value is corrected on the basis of the height of the flow path 41 measured at step S200. Consider, for example, a case where the hematocrit value is calculated with a reference value of the height of the flow path 41 set to 100 μm. In this case, when a measurement value of the height of the flow path 41 is 110 μm, the hematocrit value may be corrected so as to be a value when the height of the flow path 41 is 100 μm in consideration of a shift amount (10 μm) between the measurement value and the reference value, that is a change amount of an absorption rate (absorption amount) of the specimen corresponding to the shift amount of the height of the flow path 41.

Finally, the measurement value is corrected on the basis of the hematocrit value in a manner similar to that of the correction of the measurement value in the first embodiment (step S120). In the second embodiment, the control processing unit 270 uses the corrected hematocrit value acquired at step S219 as the hematocrit value.

By the above-described procedure, an amount (concentration) of a substance to be measured in plasma may be determined.

(Effect)

In the second embodiment, in addition to the effect of the first embodiment, the hematocrit value may be measured with a higher degree of accuracy and the amount of the substance to be measured in the plasma may be determined with a higher degree of accuracy. In the second embodiment, by correcting the hematocrit value on the basis of the height of the flow path 41, it is possible to eliminate an effect of a dimensional error when manufacturing the measurement chip 10. As a result, dimensional accuracy required for the measurement chip 10 may be reduced.

Third Embodiment

In a third embodiment also, a hematocrit value is corrected on the basis of a height of a flow path. Since a measurement system and a measurement apparatus according to the third embodiment are the same as the measurement system and measurement apparatus according to the first embodiment except an operation procedure of the measurement apparatus (measurement method), the same reference sign is assigned to the same component and the description thereof is omitted.

(Measurement System and SPFS Apparatus)

FIG. 1 is a schematic diagram illustrating a configuration of a measurement system 3 according to the third embodiment. As illustrated in FIG. 1, the measurement system 3 includes a measurement chip 10 and an SPFS apparatus 300. The SPFS apparatus 300 includes an excitation light emitting unit 110, a signal detecting unit 120, a liquid sending unit 130, a transporting unit 140, a light emitting unit 150, a light detecting unit 160, and a control processing unit (processing unit) 370.

The control processing unit 370 is similar to the control processing unit 170 according to the first embodiment except that control for measuring a height of a flow path 41 is added, so that the description thereof is omitted. Note that, in the control processing unit 370, data regarding a calibration curve for determining the height of the flow path 41 is recorded on the basis of a detection result of sixth light $\delta_6$ to be described later.

(Operation Procedure of SPFS Apparatus)

Figure 7:
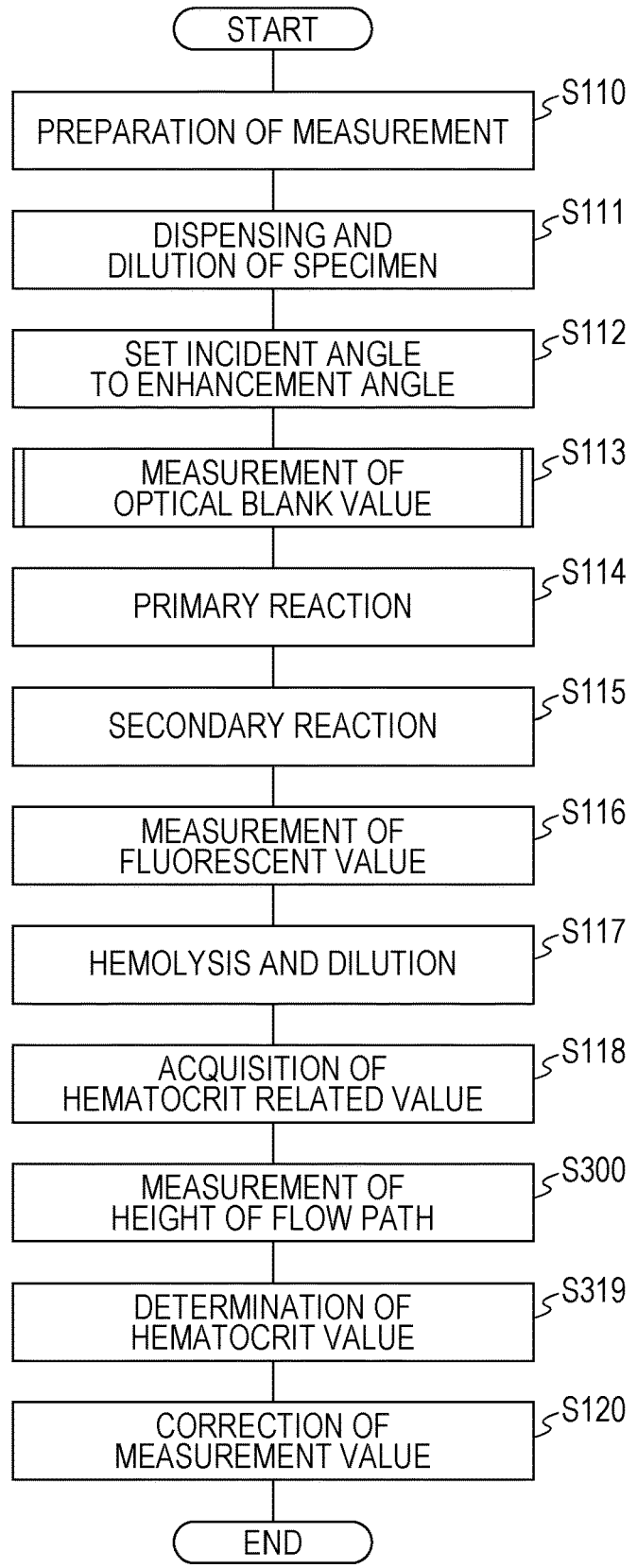
FIG. 7 is a flowchart illustrating an example of an operation procedure of the measurement system according to the third embodiment.

An operation procedure of the measurement system 3 according to the third embodiment (measurement method according to the third embodiment) is described. FIG. 7 is a flowchart illustrating an example of the operation procedure of the measurement system 3.

In a manner similar to the measurement method according to the first embodiment, steps from preparing measurement (step S110) to acquiring a hematocrit related value (step S118) are performed.

Next, the height of the flow path 41 is measured (step S300). Specifically, the control processing unit 370 controls a transporting stage 141 to move the measurement chip 10 from a second measurement position to a liquid sending position. Thereafter, the control processing unit 370 controls a pipette control unit 135 to discharge liquid in the flow path 41 and provides second liquid containing a dye which absorbs light of at least a partial wavelength of first light $\delta_1$ accommodated in a liquid chip 50. The control processing unit 370 controls the transporting stage 141 to move the measurement chip 10 from the liquid sending position to the second measurement position again. Next, the control processing unit 370 allows a second light source unit 151 to apply the first light $\delta_1$ to the metal film 30. At the same time, the control processing unit 370 controls a second sensor control unit 162 to detect the sixth light $\delta_6$ acquired when the first light $\delta_1$ passes through the second liquid in the flow path 41, is reflected by the metal film 30, and passes through the second liquid in the flow path 41 again by a second light receiving sensor 161 in a state in which the flow path 41 is filled with the second liquid. A detection result of the sixth light $\delta_6$ is transmitted to the control processing unit 370 and recorded.

The control processing unit 370 determines the height of the flow path 41 on the basis of the detection result of the sixth light $\delta_6$ by the light detecting unit 160. An optical path length of the sixth light $\delta_6$ in the second liquid changes depending on the height of the flow path 41. An absorption amount by the dye of the sixth light $\delta_6$ in the second liquid changes depending on the optical path length of the sixth light $\delta_6$ in the second liquid. Therefore, the height of the flow path 41 may be determined on the basis of a light amount of the sixth light $\delta_6$. For example, the control processing unit 370 determines the height of the flow path 41 on the basis of the calibration curve prepared in advance and the detection result (light amount) of the sixth light $\delta_6$.

Next, the hematocrit value is determined (step S319). The control processing unit 370 determines the hematocrit value of a specimen on the basis of the detection result of the light detecting unit 160. In this embodiment, the control processing unit 370 calculates the hematocrit value by multiplying the hematocrit related value acquired at step S118 by a correction coefficient recorded in the control processing unit 370 in advance. Furthermore, in the third embodiment, the hematocrit value is corrected on the basis of the height of the flow path 41 measured at step S300. Consider, for example, a case where the hematocrit value is calculated with a reference value of the height of the flow path 41 set to 100 μnm. In this case, when the measurement value of the height of the flow path 41 is 110 μm, the hematocrit value may be corrected so as to be a value when the height of the flow path 41 is 100 μm in consideration of a shift amount (10 μm) between the measurement value and the reference value, that is a change amount of an absorption rate (absorption amount) of the specimen corresponding to the shift amount of the height of the flow path 41.

Finally, the measurement value is corrected on the basis of the hematocrit value in a manner similar to that of the correction of the measurement value in the first embodiment (step S120). In the third embodiment, the control processing unit 370 uses the corrected hematocrit value acquired at step S319 as the hematocrit value.

By the above-described procedure, the amount of the substance to be measured in the plasma may be determined.

(Effect)

In the third embodiment, an effect similar to that of the second embodiment may be acquired.

[Variation]

(Variation 1)

Figure 8:
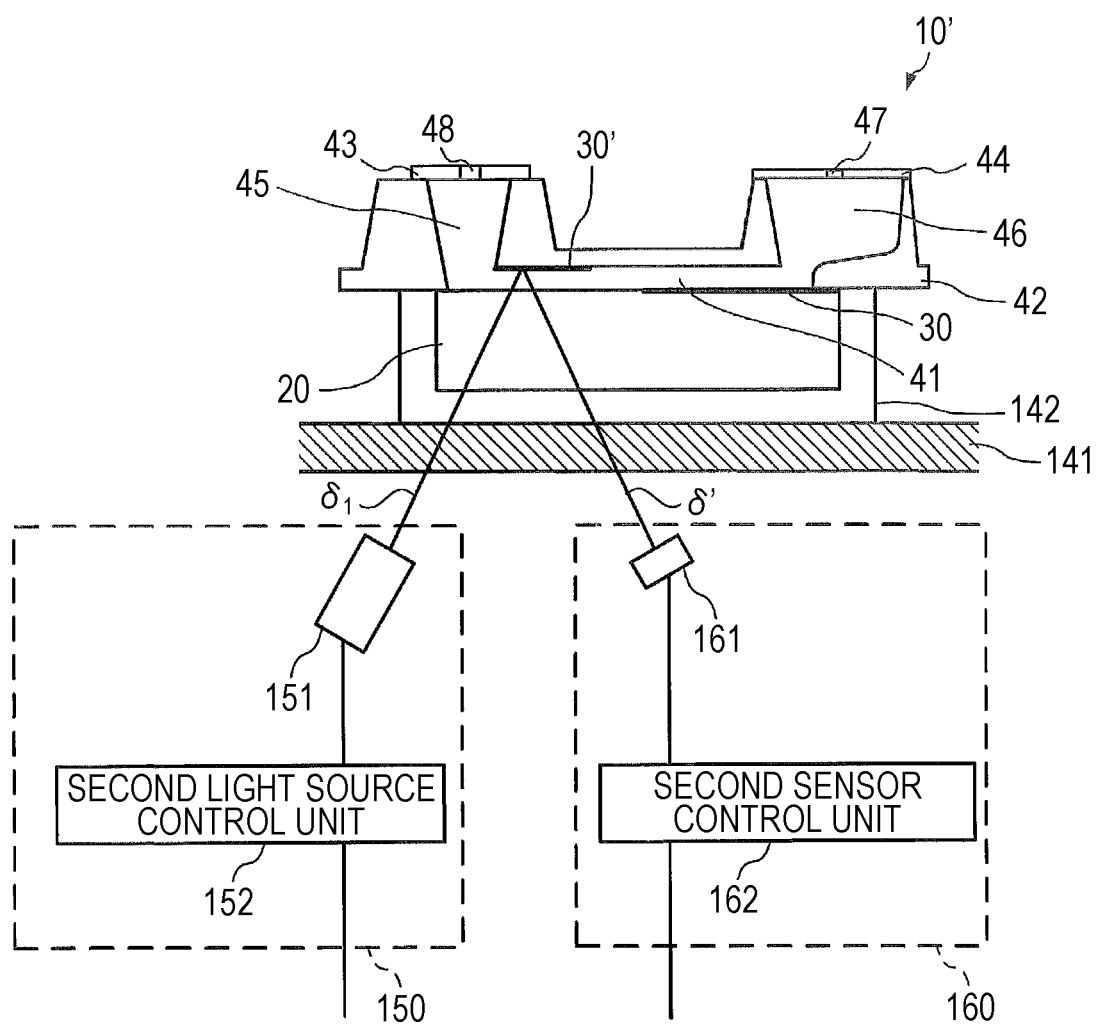
FIG. 8 is a schematic cross-sectional view illustrating a configuration of a hematocrit value acquiring unit in a measurement system according to a variation 1.

In the above-described first to third embodiment, the mode in which the first light $\delta_1$ is specularly reflected and the surface plasmon resonance occurs on the metal film 30 which is the metal film is described, but the present invention is not limited to this mode. FIG. 8 is a schematic diagram illustrating a configuration of a hematocrit value acquiring unit in a measurement system according to a variation 1. In FIG. 8, in order to illustrate an optical path in a measurement chip 10', a cross-section of the measurement chip 10' is not hatched. As illustrated in FIG. 8, a reflecting unit 30' for specularly reflecting first light $\delta_1$ and a metal film 30 on which surface plasmon occurs may be separately formed. Note that a prism 20 of the measurement chip 10' according to the variation 1 is formed of a dielectric material transparent to excitation light α and the first light $\delta_1$ (and light δ' having the same wavelength as that of the first light $\delta_1$).

In the measurement chip 10' according to the variation 1, the reflecting unit 30' is arranged so as to be opposed to the prism 20 across a flow path 41, and the metal film 30 is arranged on the prism 20. In the variation 1, the reflecting unit 30' is arranged on a bottom surface of a concave portion of a frame body 42 (top surface of the flow path 41).

A material of the reflecting unit 30' is not especially limited as long as this is metal capable of specularly reflecting light on a surface thereof. Examples of the material of the reflecting unit 30' include gold, silver, copper, aluminum, and alloys thereof. In the variation 1, the reflective unit 30' is a gold thin film. Although a thickness of the reflecting unit 30' is not especially limited, this is preferably within a range of 20 nm to 10 μm. A method of forming the reflecting unit 30' is not especially limited. Examples of the method of forming the reflecting unit 30' include sputtering, vapor deposition, and plating.

In the variation 1, a light emitting unit 150 emits the first light $\delta_1$ from a side of the prism 20 toward the reflecting unit 30'. When the light emitting unit 150 emits the first light $\delta_1$ from the prism 20 side toward the reflecting unit 30', a light detecting unit 160 detects light acquired when the first light $\delta_1$ passes through the flow path 41, is reflected by the reflecting unit 30', and passes through the flow path 41 again.

(Variation 2)

Figure 9:
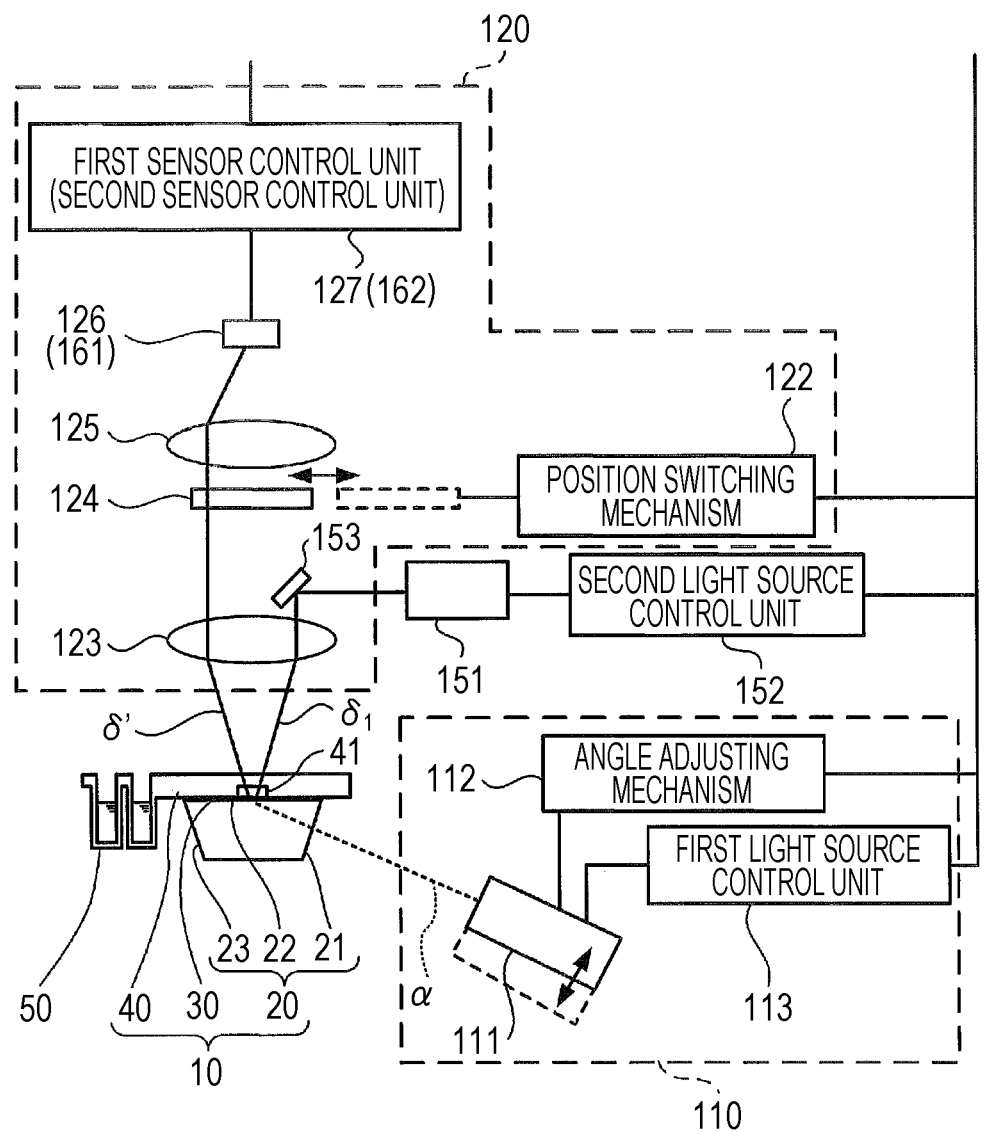
FIG. 9 is a schematic diagram illustrating a configuration of a measurement value acquiring unit and a hematocrit value acquiring unit in a measurement system according to a variation 2.

In the first to third embodiments described above, the mode in which the measurement value acquiring unit and the hematocrit value measuring unit are separated is described, but the present invention is not limited to this mode. FIG. 9 is a schematic diagram illustrating a configuration of a measurement value acquiring unit and a hematocrit value acquiring unit in a measurement system according to a variation 2. As illustrated in FIG. 9, the measurement value acquiring unit and the hematocrit value acquiring unit may be integrally configured. An SPFS apparatus according to the variation 2 may have another optical element as necessary. The SPFS apparatus according to the variation 2 includes a mirror 153 for reflecting first light $\delta_1$ from a second light source unit 151.

In the SPFS apparatus according to the variation 2, optical lenses (first lens 123 and second lens 125) for condensing a signal of a signal detecting unit 120 also serves as optical lenses for guiding the first light $\delta_1$ to a metal film 30 and guiding reflected light $\delta'$ (for example, second light $\delta_2$) of the first light $\delta_1$ in a measurement chip 10 to a light receiving element. The light receiving element (first light receiving sensor 126) for detecting the signal also serves as a second light receiving sensor 161 for receiving the reflected light $\delta'$ (for example, the second light $\delta_2$) of the first light $\delta_1$ in the measurement chip 10. In this manner, it is preferable that the measurement value acquiring unit and the hematocrit value measuring unit are integrally configured from a viewpoint of reducing a cost of the measurement apparatus and miniaturizing the measurement apparatus. In addition, since movement between a first measurement position and a second measurement position becomes unnecessary, measurement time may be shortened. Note that in the variation 2, an optical filter 124 may be transparent to the light $\delta'$ or not transparent to the light $\delta'$. In a case where the optical filter 124 is not transparent to the light $\delta'$, the optical filter 124 is retracted out of an optical path when detecting the light $\delta'$.

Also, the configurations of the measurement apparatuses 200 and 300 according to the above-described second and third embodiments are not limited to the above-described modes. Although a case of using the light receiving sensor the same as the second light receiving sensor 161 or 261 which receives the second light $\delta_2$ as the light receiving sensor for receiving the light (third light $\delta_3$, fourth light $\delta_4$, sixth light $\delta_6$, and ninth light $\delta_9$) for measuring the height of the flow path 41 is described in the measurement apparatuses 200 and 300 according to the second and third embodiments described above, the present invention is not limited to this mode. The light receiving sensor for receiving the light for measuring the height of the flow path 41 described above and the second light receiving sensor for receiving the second light $\delta_2$ may be different from each other. From a viewpoint of avoiding an increase in size of the measurement apparatus, the light receiving sensor for receiving the light for measuring the height of the flow path 41 described above and the light receiving sensor for receiving the second light $\delta_2$ are preferably the same.

Also, in the second and third embodiments described above, the same light source unit (second light source unit 151) is used when measuring the height of the flow path 41 and measuring the hematocrit value, but the light source unit to be used may be different.

Also, in a case of measuring the height of the flow path 41, it is not necessary to use the hematocrit value measuring unit of the measurement apparatuses 200 and 300. For example, another optical apparatus such as a laser displacement meter may be prepared.

In addition, although the mode of measuring the height of the flow path 41 is described in the above-described second and third embodiments, the present invention is not limited to this mode. Information regarding the height of the flow path 41 may be measured in advance at the time of manufacturing the measurement chip. The information regarding the height of the flow path 41 may be recorded in advance in the control processing units 270 and 370 or may be attached to the measurement chip as an identifier such as a barcode. As a result, when measuring the amount of the substance to be measured, it is not necessary to measure the height of the flow path 41, so that the measurement time (diagnosis time) of the substance to be measured may be shortened.

Also, in the second and third embodiments described above, the mode in which the hematocrit value is corrected on the basis of the height of the flow path 41 is described; however, it is also possible to correct the hematocrit value on the basis of the optical path length in the flow path 41 of the light which becomes the second light $\delta_2$ in place of the height of the flow path 41.

Furthermore, although the mode in which the SPSF method is used and the fluorescence value of the fluorescence $\beta$ from the fluorescent substance is measured as the measurement value is described in the above-described first to third embodiments, the present invention is not limited to this mode. For example, it is also possible to measure the light amount of the reflected light of the excitation light $\alpha$ as the measurement value by utilizing an SPR method. Alternatively, in the present invention, the measurement value may be acquired by using an ELISA method, an RIfS method, a QCM method or the like.

The present application claims priority based on JP 2016-160753 A filed on Aug. 18, 2016. The contents described in the specification and drawings of the application are entirely incorporated herein by reference.

INDUSTRIAL APPLICABILITY

The measurement method, measurement apparatus, and measurement system of the substance to be measured according to the present invention may detect the substance to be measured with high reliability, so that they are useful for examining diseases, for example.

REFERENCE SIGNS LIST 1, 2, 3 Measurement system
10, 10' Measurement chip
20 Prism
21 Incident surface
22 Film depositing surface
23 Emitting surface
30 Metal film
30' Reflecting unit
40 Flow path lid
41 Flow path
42 Frame body
43 Liquid injecting unit covering film
44 Liquid storage unit covering film
45 Liquid injecting unit
46 Liquid storage unit
47 Vent hole
48 Pipette chip through hole
50 Liquid chip
100, 200, 300 SPFS apparatus
110 Excitation light emitting unit (second light emitting unit)
111 First light source unit
112 Angle adjusting mechanism
113 First light source control unit
120 Signal detecting unit
121 Light receiving optical system unit
122 Position switching mechanism
123 First lens
124 Optical filter 125 Second lens
126 First light receiving sensor
127 First sensor control unit
130 Liquid sending unit
131 Pipette
132 Syringe pump
133 Nozzle unit
134 Pipette chip
135 Pipette control unit
140 Transporting unit
141 Transporting stage
142 Chip holder
150 Light emitting unit
151 Second light source unit
152 Second light source control unit
153 Mirror
160, 260 Light detecting unit
161, 261 Second light receiving sensor
162 Second sensor control unit
170, 270, 370 Control processing unit
α Excitation light (eighth light)
β Fluorescence
γ Plasmon scattered light
$\delta_1$ First light
δ' Reflected light of first light in measurement chip
$\delta_2$ Second light
$\delta_3$ Third light
$\delta_4$ Fourth light
$\delta_5$ Fifth light
$\delta_7$ Seventh light
$\delta_9$ Ninth light

The invention claimed is:

1. A measurement method for measuring an amount of a substance to be measured in a specimen containing blood, the measurement method comprising:
introducing the specimen containing the substance to be measured into a flow path of a measurement chip including the flow path which is a cavity for accommodating liquid and a reflecting part for specularly reflecting light which passes through the flow path so as to pass through the flow path again, and acquiring a measurement value indicating the amount of the substance to be measured in the specimen;
detecting second light acquired when first light including light of a wavelength absorbed by a red blood cell passes through the specimen in the flow path, is reflected by the reflecting part, and passes through the specimen in the flow path again in a state in which the specimen is present in the flow path;
determining a hematocrit value of the specimen on the basis of a detection result of the second light and at least one of an optical path length in the flow path of light which becomes the second light or a height of the flow path; and
correcting the measurement value on the basis of the hematocrit value.

2. The measurement method according to claim 1, wherein the determining the hematocrit value includes correcting the hematocrit value on the basis of a wavelength of the first light and at least one of the optical path length in the flow path of light which becomes the second light or the height of the flow path.

3. The measurement method according to claim 1, further comprising:
detecting third light acquired when the first light passes through the flow path, is reflected by the reflecting part, and passes through the flow path again, and fourth light acquired when the first light is reflected by a surface opposed to the reflecting part of the flow path by an array sensor in a first state in which the flow path is a cavity;
detecting fifth light acquired when the first light passes through first liquid in the flow path, is reflected by the reflecting part, and passes through the first liquid in the flow path again by an array sensor in a second state in which the flow path is filled with the first liquid transparent to the first light; and
determining the optical path length in the flow path of the light which becomes the second light or the height of the flow path on the basis of detection results of the third light, the fourth light, and the fifth light.

4. The measurement method according to claim 1, further comprising:
detecting sixth light acquired when the first light passes through second liquid in the flow path, is reflected by the reflecting part, and passes through the second liquid in the flow path again in a state in which the flow path is filled with the second liquid containing a dye which absorbs light of at least a partial wavelength of the first light; and
determining the optical path length in the flow path of the light which becomes the second light or the height of the flow path on the basis of a detection result of the sixth light.

5. The measurement method according to claim 1, wherein at the determining the hematocrit value, the hematocrit value is determined on the basis of a detection result of the second light which passes through the specimen in a state in which blood is hemolyzed.

6. The measurement method according to claim 1, further comprising:
detecting seventh light acquired when the first light passes through reference liquid in the flow path, is reflected by the reflecting part, and passes through the reference liquid in the flow path again in a state in which the reference liquid transparent to the first light is present in the flow path,
wherein at the determining the hematocrit value, the hematocrit value determined on the basis of the detection result of the second light is corrected on the basis of a detection result of the seventh light.

7. The measurement method according to claim 1, wherein at the detecting the second light, the first light is applied to the reflecting part such that a plane including an optical axis of the first light and an optical axis of the second light is in a longitudinal direction of the flow path.

8. The measurement method according to claim 1,
wherein the measurement chip includes a prism, a metal film arranged on the prism, the flow path arranged on the metal film, and the reflecting part arranged so as to be opposed to the prism across the flow path,
at the acquiring the measurement value, the measurement value is acquired by detecting a signal indicating the amount of the substance to be measured generated when eighth light is applied at an incident angle at which surface plasmon resonance occurs to the metal film via the prism in a state in which the substance to be measured contained in the specimen is immobilized and the specimen is not present on the metal film, and
at the detecting the second light, the first light is applied from a side of the prism toward the reflecting part in a state in which the specimen is present in the flow path.

9. The measurement method according to claim 1,
wherein the measurement chip includes a prism, the reflecting part which is a metal film arranged on the prism, and the flow path arranged on the reflecting part,
at the acquiring the measurement value, the measurement value is acquired by detecting a signal indicating the amount of the substance to be measured generated when eighth light is applied at an incident angle at which surface plasmon resonance occurs to the reflecting part via the prism in a state in which the substance to be measured contained in the specimen is immobilized and the specimen is not present on the reflecting part, and
at the detecting the second light, the first light is applied from a side of the flow path to the reflecting part in the state in which the specimen is present in the flow path.

10. A measurement apparatus for measuring an amount of a substance to be measured in a specimen containing blood, the measurement apparatus comprising:
a chip holder for holding a measurement chip including a flow path which is a cavity for accommodating liquid, and a reflecting part for specularly reflecting light which passes through the flow path so as to pass through the flow path again;
a measurement value acquiring part for acquiring a measurement value indicating the amount of the substance to be measured in the specimen in a state in which the substance to be measured in the specimen is present in the flow path of the measurement chip held by the chip holder;
a light emitting part for emitting first light including light of a wavelength absorbed by a red blood cell;
a light detecting part for detecting second light acquired when the first light passes through the specimen in the flow path, is reflected by the reflecting part, and passes through the specimen in the flow path again when the light emitting part emits the first light toward the reflecting part in a state in which the specimen is present in the flow path; and
a processing part which determines a hematocrit value of the specimen on the basis of a detection result of the second light by the light detecting part and at least one of an optical path length in the flow path of light which becomes the second light or a height of the flow path, and corrects the measurement value on the basis of the hematocrit value.

11. The measurement apparatus according to claim 10, wherein the processing part corrects the hematocrit value on the basis of a wavelength of the first light and at least one of the optical path length in the flow path of light which becomes the second light or the height of the flow path.

12. The measurement apparatus according to claim 10,
wherein the light detecting part includes an array sensor for receiving the second light,
the light detecting unit:
detects third light acquired when the first light passes through the flow path, is reflected by the reflecting part, and passes through the flow path again, and fourth light acquired when the first light is reflected by a surface opposed to the reflecting part of the flow path when the light emitting part emits the first light toward the reflecting part in a state in which the flow path is a cavity; and
detects fifth light acquired when the first light passes through first liquid in the flow path, is reflected by the reflecting part, and passes through the first liquid in the flow path again when the light emitting part emits the first light toward the reflecting part in a state in which the flow path is filled with the first liquid transparent to the first light, and
the processing part determines the optical path length in the flow path of the light which becomes the second light or the height of the flow path on the basis of detection results of the third light, the fourth light, and the fifth light by the array sensor.

13. The measurement apparatus according to claim 10,
wherein the light detecting part detects sixth light acquired when the first light passes through second liquid in the flow path, is reflected by the reflecting part, and passes through the second liquid in the flow path again when the light emitting part emits the first light toward the reflecting part in a state in which the flow path is filled with the second liquid containing a dye which absorbs light of at least a partial wavelength of the first light, and
the processing part determines the optical path length in the flow path of the light which becomes the second light or the height of the flow path on the basis of a detection result of the sixth light by the light detecting part.

14. The measurement apparatus according to claim 10, wherein the processing part determines the hematocrit value on the basis of the detection result of the second light which passes through the specimen in a state in which blood is hemolyzed.

15. The measurement apparatus according to claim 10,
wherein the light detecting part detects seventh light acquired when the first light passes through reference liquid in the flow path, is reflected by the reflecting part, and passes through the reference liquid in the flow path again when the light emitting part emits the first light toward the reflecting part in a state in which the reference liquid transparent to the first light is present in the flow path, and
the processing part corrects the hematocrit value on the basis of a detection result of the seventh light.

16. The measurement apparatus according to claim 10, wherein the light emitting part and the light detecting part are arranged such that a plane including an optical axis of the first light and an optical axis of the second light is in a longitudinal direction of the flow path.

17. The measurement apparatus according to claim 10,
wherein the measurement chip includes a prism, a metal film arranged on the prism, the flow path arranged on the metal film, and the reflecting part arranged so as to be opposed to the prism across the flow path,
the measurement value acquiring part includes:
a second light emitting part for emitting eighth light; and
a signal detecting part for detecting a signal indicating the amount of the substance to be measured generated when the second light emitting part emits the eighth light at an incident angle at which surface plasmon resonance occurs toward the metal film via the prism in a state in which the substance to be measured contained in the specimen is immobilized and the specimen is not present on the metal film,
the light emitting part emits the first light from a side of the prism toward the reflecting part, and
the processing part acquires the measurement value on the basis of a detection result of the signal detecting part.

18. The measurement apparatus according to claim 10,
wherein the measurement chip includes a prism, the reflecting part which is a metal film arranged on the prism, and the flow path arranged on the reflecting part, the measurement value acquiring part includes:

a second light emitting part for emitting eighth light; and a signal detecting part for detecting a signal indicating the amount of the substance to be measured generated when the second light emitting part emits the eighth light at an incident angle at which surface plasmon resonance occurs toward the metal film via the prism in a state in which the substance to be measured contained in the specimen is immobilized and the specimen is not present on the metal film, the light emitting part emits the first light from a side of the flow path toward the reflecting part, and the processing part acquires the measurement value on the basis of a detection result of the signal detecting part.

19. The measurement apparatus according to claim 18, wherein the signal detecting part includes an optical lens for condensing the signal, and a light receiving element for receiving the signal, the optical lens also serves as an optical lens which guides the first light to the reflecting part and guides the second light to the light receiving element, and the light receiving element also serves as a light receiving element for receiving the second light.

20. A measurement system for measuring an amount of a substance to be measured in a specimen containing blood, the measurement system comprising:

a measurement chip including a flow path which is a cavity for accommodating liquid, and a reflecting part for specularly reflecting light which passes through the flow path so as to pass through the flow path again;

a measurement value acquiring part for acquiring a measurement value indicating the amount of the substance to be measured in the specimen in a state in which the substance to be measured in the specimen is present in the flow path;

a light emitting part for emitting first light including light of a wavelength absorbed by a red blood cell;

a light detecting part for detecting second light acquired when the first light passes through the specimen in the flow path, is reflected by the reflecting part, and passes through the specimen in the flow path again when the light emitting part emits the first light toward the reflecting part in a state in which the specimen is present in the flow path; and a processing part which determines a hematocrit value of the specimen on the basis of a detection result of the second light by the light detecting part and at least one of an optical path length in the flow path of light which becomes the second light or a height of the flow path, and corrects the measurement value on the basis of the hematocrit value.

* * * * *